(12) United States Patent
Pham et al.

(10) Patent No.: US 11,007,057 B2
(45) Date of Patent: May 18, 2021

(54) HEART VALVE LEAFLET REPLACEMENT SYSTEM AND METHOD FOR SAME

(71) Applicant: Dura LLC, East Windsor, CT (US)

(72) Inventors: Thuy Pham, Manchester, CT (US); Caitlin Martin, Atlanta, GA (US); Qian Wang, Manchester, CT (US)

(73) Assignee: DURA LLC, Marietta, GA (US)

( * ) Notice: Subject to any disclaimer, the term of this patent is extended or adjusted under 35 U.S.C. 154(b) by 0 days.

(21) Appl. No.: 15/453,518

(22) Filed: Mar. 8, 2017

(65) Prior Publication Data

US 2017/0258589 A1 Sep. 14, 2017

Related U.S. Application Data

(60) Provisional application No. 62/305,204, filed on Mar. 8, 2016, provisional application No. 62/413,693, filed
(Continued)

(51) Int. Cl.
*A61F 2/24* (2006.01)
*A61B 17/04* (2006.01)
*A61B 17/06* (2006.01)

(52) U.S. Cl.
CPC ........ *A61F 2/2445* (2013.01); *A61B 17/0401* (2013.01); *A61B 17/0487* (2013.01);
(Continued)

(58) Field of Classification Search
CPC .... A61F 2/2445; A61F 2/2448; A61F 2/2463; A61F 2/24; A61F 2/2409; A61F 2/2418;
(Continued)

(56) References Cited

U.S. PATENT DOCUMENTS 8,845,717 B2    9/2014   Khairkhahan et al.
8,888,843 B2   11/2014   Khairkhahan et al.
(Continued)

FOREIGN PATENT DOCUMENTS

CN    103687574 A    3/2014
CN    104768500 A    7/2015
(Continued)

OTHER PUBLICATIONS

Pham, Thuy; International Search Report and Written Opinion for PCT Application No. PCT/US2017/021369, filed Mar. 8, 2017, dated May 26, 2017, 12 pgs.
(Continued)

*Primary Examiner* — Christopher D. Prone
(74) *Attorney, Agent, or Firm* — William A. English; Vista IP Law Group LLP

(57) ABSTRACT

A prosthetic heart valve for treatment of a diseased heart valve having native anterior and posterior leaflets that move between an open configuration and a closed position to regulate blood flow through the heart valve during a cardiac cycle of a heart. The prosthetic heart valve having a crescent shaped stent, at least one prosthetic leaflet mounted on an inner surface of the stent, and at least one prong structure coupling a portion of the at least one prosthetic leaflet to a lower ventricular portion of the stent frame. The prosthetic heart valve further having systems for anchoring the upper flared portion of the stent to a posterior portion of the native valve annulus.

31 Claims, 34 Drawing Sheets

Related U.S. Application Data on Oct. 27, 2016, provisional application No. 62/427,551, filed on Nov. 29, 2016.

(52) U.S. Cl.
CPC .............. *A61F 2/243* (2013.01); *A61F 2/246* (2013.01); *A61F 2/2418* (2013.01); *A61F 2/2463* (2013.01); *A61B 2017/0409* (2013.01); *A61B 2017/0414* (2013.01); *A61B 2017/0441* (2013.01); *A61B 2017/0464* (2013.01); *A61B 2017/06176* (2013.01); *A61F 2/2466* (2013.01); *A61F 2220/0008* (2013.01); *A61F 2230/0013* (2013.01); *A61F 2230/0067* (2013.01); *A61F 2230/0069* (2013.01)

(58) Field of Classification Search
CPC .. A61F 2203/0013; A61F 2/243; A61F 2/246; A61F 2/26; A61F 2230/0067; A61F 2230/0069

See application file for complete search history.

(56) References Cited

U.S. PATENT DOCUMENTS

| | | | |
|---|---|---|---|
| 9,232,996 B2* | 1/2016 | Sun | A61F 2/2412 |
| 2004/0122513 A1 | 6/2004 | Navia | |
| 2004/0236419 A1* | 11/2004 | Milo | A61B 17/0401 623/2.36 |
| 2007/0244558 A1 | 10/2007 | Machiraju | |
| 2008/0234702 A1 | 9/2008 | Marales | |
| 2014/0067048 A1* | 3/2014 | Chau | A61F 2/246 623/2.1 |
| 2014/0128965 A1 | 5/2014 | Rafiee | |
| 2014/0155995 A1 | 6/2014 | Sun et al. | |
| 2014/0163668 A1 | 6/2014 | Rafiee | |
| 2014/0309727 A1 | 10/2014 | Lamelas | |
| 2014/0358223 A1 | 12/2014 | Rafiee et al. | |
| 2015/0088248 A1 | 3/2015 | Scorsin et al. | |
| 2015/0119981 A1* | 4/2015 | Khairkhahan | A61F 2/2442 623/2.36 |
| 2015/0216660 A1 | 8/2015 | Pintor | |

FOREIGN PATENT DOCUMENTS

| | | |
|---|---|---|
| WO | 2015052570 | 4/2015 |
| WO | 2017156133 | 9/2017 |

OTHER PUBLICATIONS

Supplementary European Search Report dated Oct. 18, 2019 for Application No. EP 17 76 4000 (8 pages).

* cited by examiner

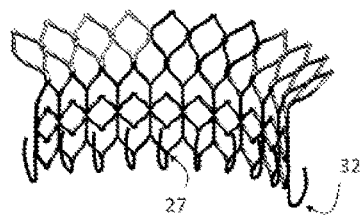 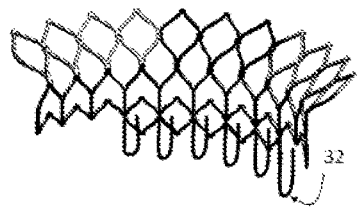 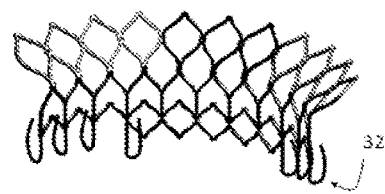
FIG. 7A     FIG. 7B     FIG. 7C
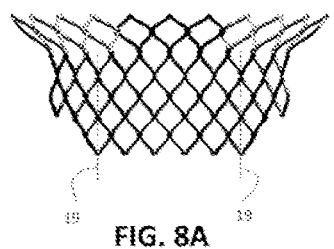 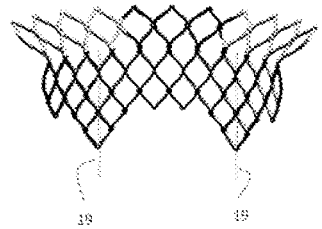
FIG. 8A     FIG. 8B
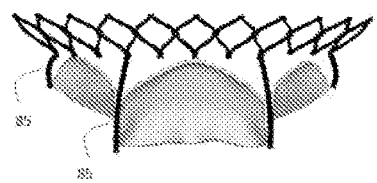 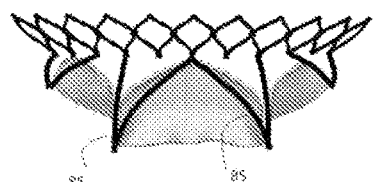 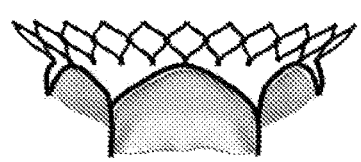
FIG. 8C     FIG. 8D     FIG. 8E

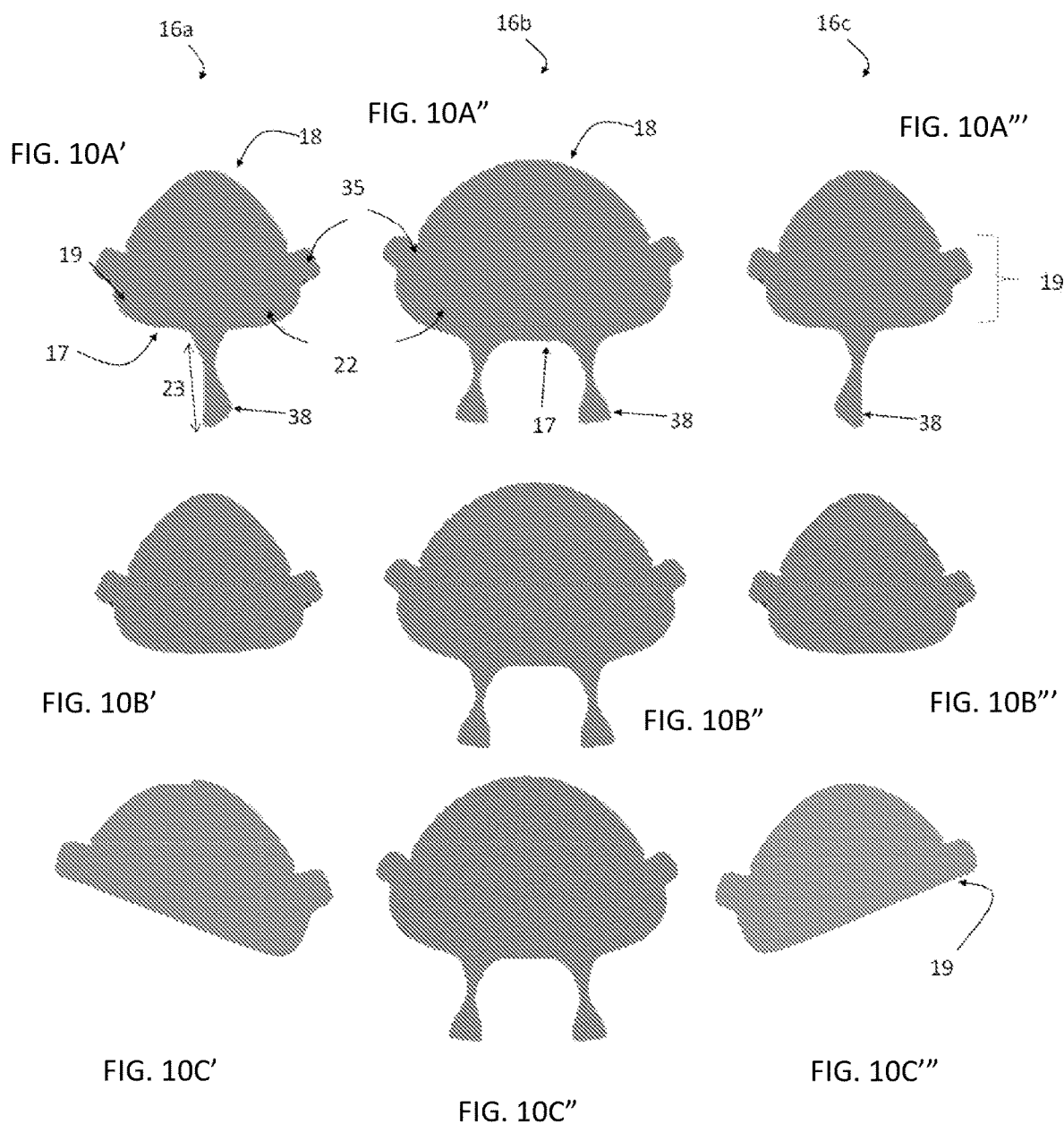

FIG. 14A
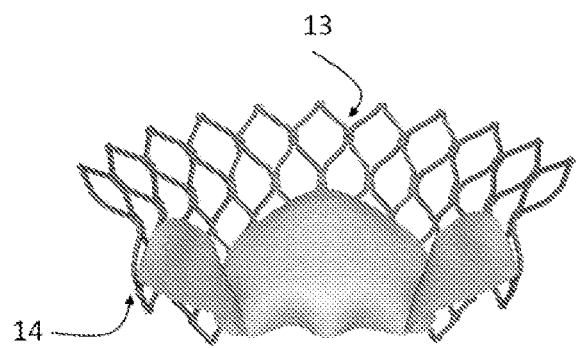
FIG. 14B
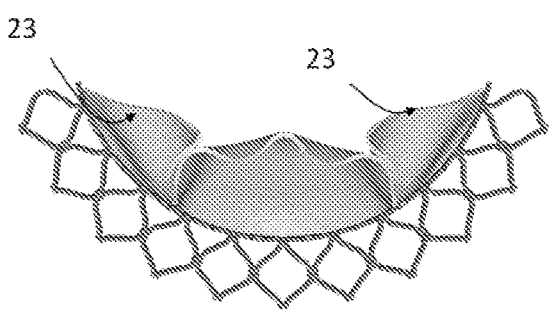
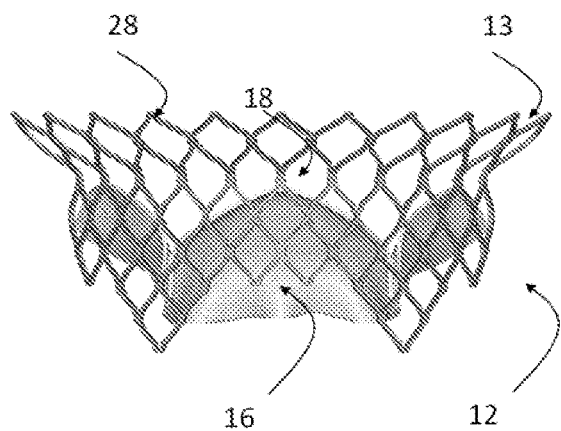
FIG. 14C

| | EXEMPLARY VALVE SIZE | |
|---|---|---|
| | # 1 | # 2 |
| SEPTAL-LATERAL (MM) | 42.00 | 37.50 |
| ANTERIOR-POSTERIOR (MM) | 16.00 | 14.00 |
| AVERAGE DIAMETER (MM) | 29.00 | 25.75 |
| AVERAGE RADIUS (MM) | 14.50 | 12.88 |
| CALCULATED AREA (MM$^2$) | 660.52 | 520.77 |
| LV PRESSURE (MMHG) | 140.00 | 140.00 |
| FORCE (N) | 12.33 | 9.72 |
| EACH ANCHOR FORCE (3 ANCHORS) | | |
| (N) | 4.11 | 3.24 |
| EACH ANCHOR FORCE (5 ANCHORS) | | |
| (N) | 2.47 | 1.94 |
| EACH ANCHOR FORCE (7 ANCHORS) | | |
| (N) | 1.76 | 1.39 |
| EACH ANCHOR FORCE (10 ANCHORS) | | |
| (N) | 1.23 | 0.97 |

FIG. 18A    FIG. 18B    FIG. 18C
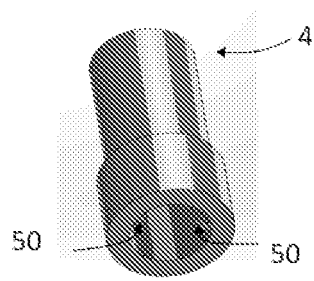 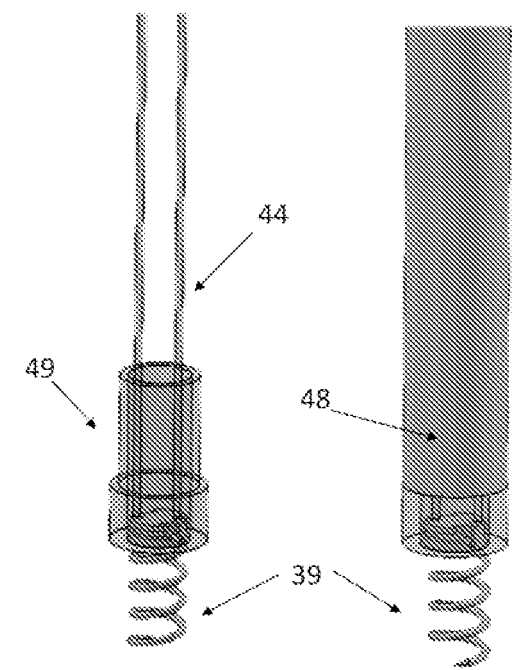
FIG. 18

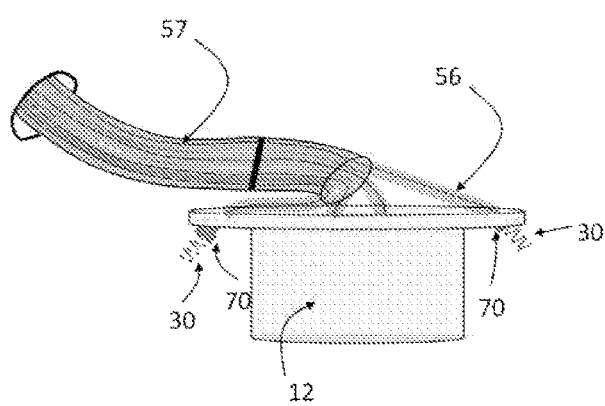
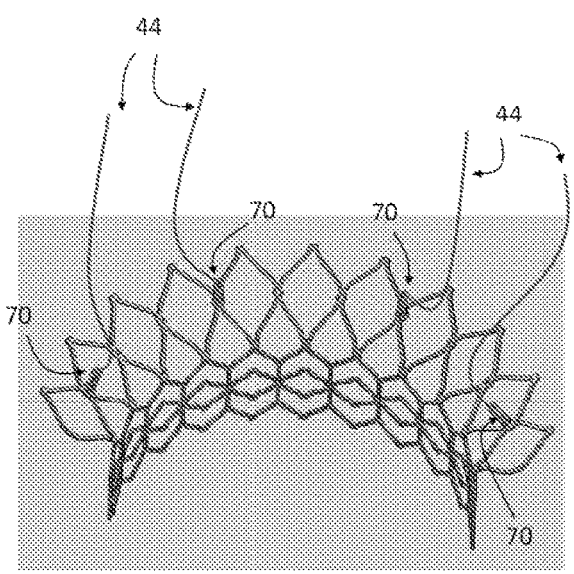
FIG. 45A
FIG. 45B

FIG. 51A
FIG. 51B
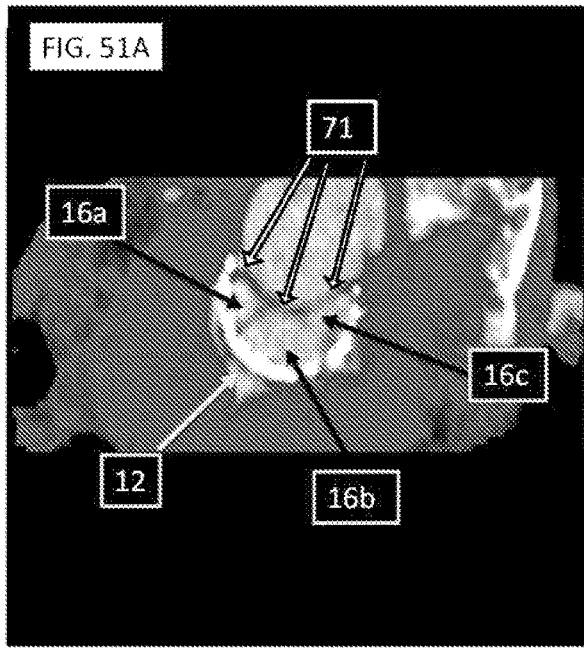
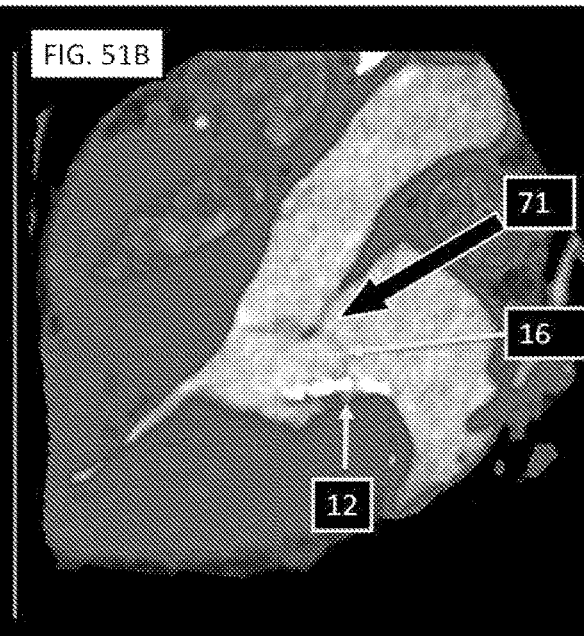
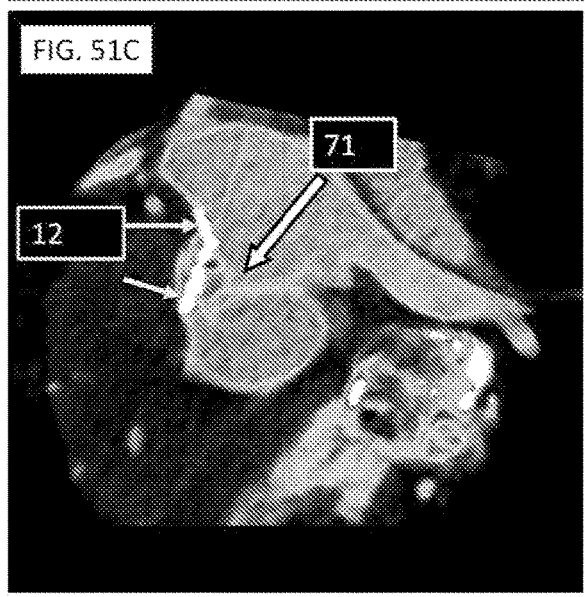
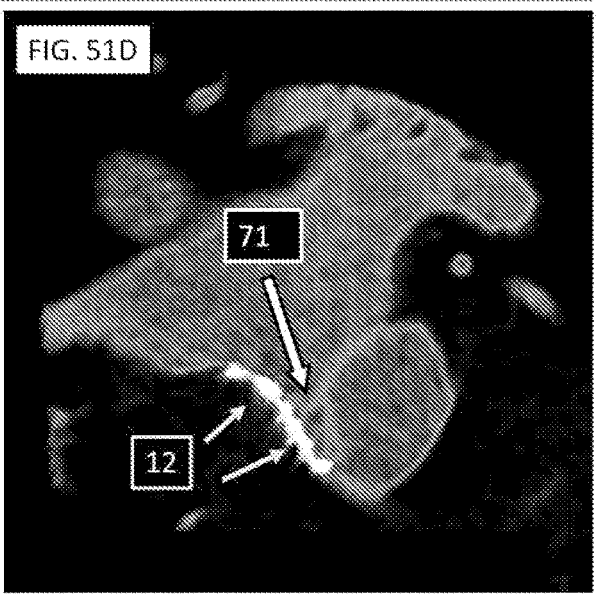
FIG. 51C
FIG. 51D

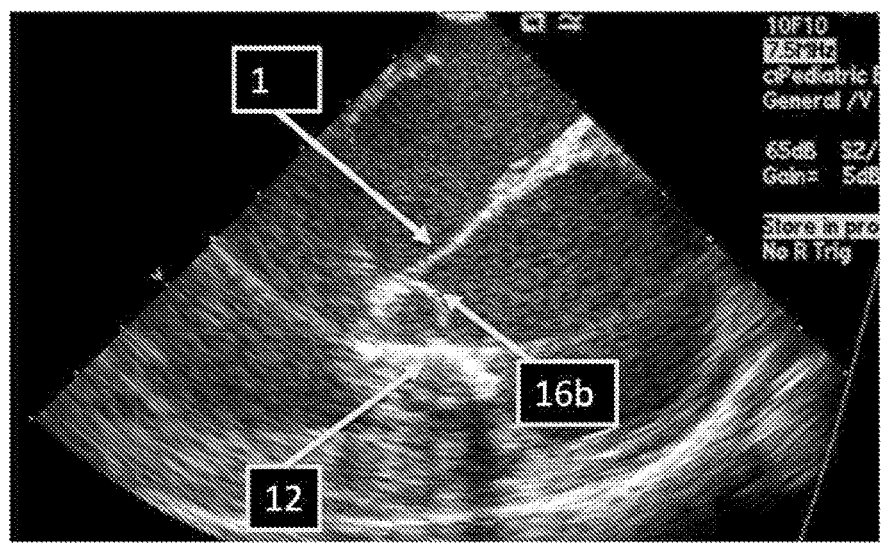
FIG. 52
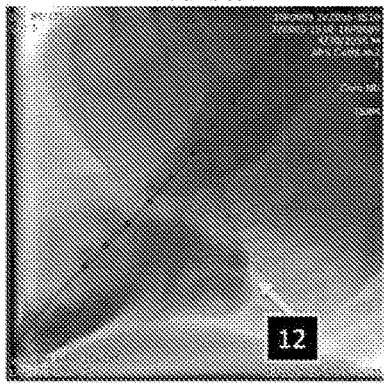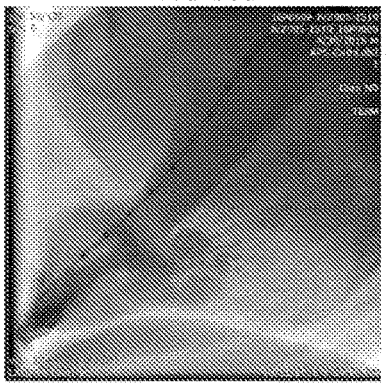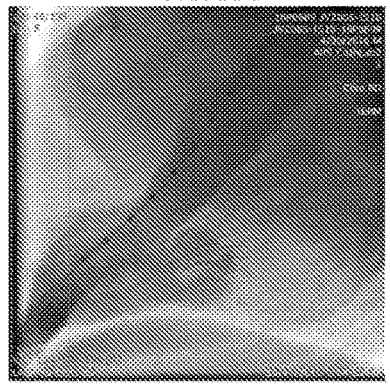
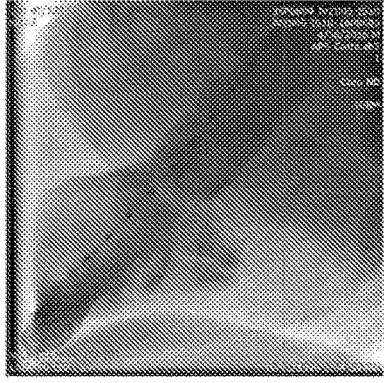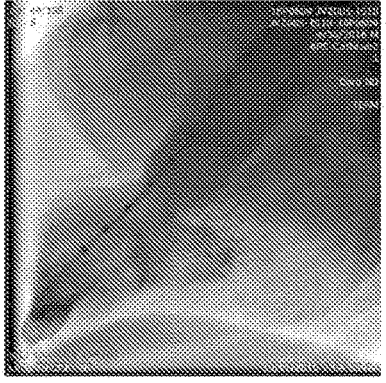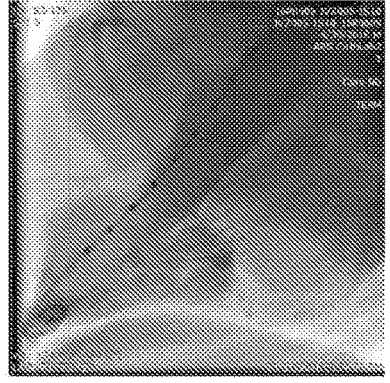

HEART VALVE LEAFLET REPLACEMENT SYSTEM AND METHOD FOR SAME

CROSS REFERENCE TO RELATED APPLICATIONS

This application claims the benefit of U.S. provisional application No. 62/305,204, filed Mar. 8, 2016, and U.S. provisional application No. 62/413,693, filed Oct. 27, 2016, and U.S. provisional application No. 62/427,551, filed Nov. 29, 2016.

FIELD

The application relates generally to replacement heart valves, preferably for replacing diseased mitral and/or tricuspid valve leaflets. More particularly, embodiments of the subject matter relate to tissue-based replacement heart valves and systems and methods to operatively deliver the replacement valve.

BACKGROUND

Referring to FIG. 1, the mitral valve (MV) sits between the left atrium (LA) and the left ventricle (LV) of a human heart and normally consists of a mitral annulus (MA), two leaflets, chordae tendineae ("chords"), two papillary muscles, and the left ventricular myocardium. The mitral annulus is subdivided into an anterior portion and a posterior portion. Normally, the anterior mitral leaflet (AML) is connected to the aortic valve via the aortic-mitral curtain, and the posterior mitral leaflet (PML) is hinged on the posterior mitral annulus. The chords originate from either the two major papillary muscles (PPM) or from multiple small muscle bundles attaching to the ventricular wall and connect to the free edge of the mitral leaflets. Chords are composed mainly of collagen bundles, which give the chords high stiffness and maintain minimal extension to prevent the leaflets from billowing into the left atrium during systole. Furthermore, a normal mitral valve consists of right and left trigones, which are two thickened regions that consist of fibrous tissues. The right fibrous trigone is between the aortic ring and the right atrioventricular ring and the left fibrous trigone is between the aortic ring and the left atrioventricular ring.

When the mitral valve is closed, the respective anterior and posterior leaflets are in close contact to form a single zone of apposition. As one skilled in the art will appreciate, normal mitral valve function involves a proper force balance, with each of its components working congruently during a cardiac cycle. Pathological alterations affecting any of the components of the mitral valve, such as chord rupture, annulus dilatation, papillary muscle displacement, leaflet calcification, and myxomatous disease, can lead to altered mitral valve function and cause mitral valve regurgitation (MR).

Mitral regurgitation is dysfunction of the mitral valve that causes an abnormal leakage of blood from the left ventricle back into the left atrium during systole (i.e., the expulsion phase of the heart cycle in which blood moves from the left ventricle into the aorta). While trivial mitral regurgitation can be present in healthy patients, moderate to severe mitral regurgitation is one of the most prevalent forms of heart valve disease. The most common causes of mitral regurgitation include ischemic heart diseases, non-ischemic heart diseases, and valve degeneration. Both ischemic (mainly due to coronary artery diseases) and non-ischemic (idiopathic dilated cardiomyopathy for example) hearts diseases can cause functional, or secondary, mitral regurgitation through various mechanisms, including impaired left ventricle wall motion, left ventricle dilatation, and papillary muscle displacement and dysfunction. In functional mitral regurgitation, the mitral valve apparatus remains normal. Incomplete coaptation of the leaflets is due to enlargement of the mitral annulus secondary to left ventricle dilation and possibly left atrium enlargement. In addition, patients with functional mitral regurgitation can exhibit papillary muscle displacement due to the left ventricle enlargement, which results in excessive tethering of the leaflets. In contrast, degenerative (or organic) mitral regurgitation is caused by structural abnormalities of the mitral leaflets and/or the subvalvular apparatus, which can include stretching or rupture of tendinous chords.

The current treatments for mitral valve diseases include surgical repair and replacement of the mitral valve. Mitral valve repair, benefiting from improved understanding of mitral valve mechanics and function, may be now preferred to complete mitral valve replacement. However, the complex physiology and three-dimensional anatomy of the mitral valve and its surrounding structure present substantial challenges when performing these repair procedures.

In one early example of a transcatheter mitral valve replacement device, Endovalve-Herrmann (Micro Interventional Devices, Inc.), developed a mitral prosthesis that had a foldable Nitinol-based valve with a sealing skirt. Similarly, Tendyne Holdings, Inc. produces a prosthetic mitral valve replacement device comprising bovine pericardium with a self-expandable Nitinol stent. The device is designed for transapical delivery and has a ventricular fixing anchor. CardiAQ uses bovine pericardium with a Nitinol self-expandable stent in their mitral valve replacement device. Finally, Tiara (Neovasc, Inc.) uses a mitral valve replacement system that is deliverable trans-apically with a 30 Fr catheter that has anchor structures, and bovine pericardium on a self-expandable stent with a D-shaped atrial portion and a ventricular portion that has an outer coating. These devices and the techniques to deliver the mitral prosthesis into the operative position are still at development stages and, though promising, challenges to the efficacy of these devices continue to exist.

The noted challenges to an efficacious mitral valve replacement device generally include operative delivery challenges; positioning and fixation challenges; seal and paravalvular leakage challenges; and hemodynamic function challenges such as left ventricle outflow tract (LVOT) obstruction. With respect to the noted operative delivery challenges, since a conventional mitral prosthetic is larger than a conventional aortic prosthesis, it is more difficult to fold and compress the larger mitral prosthesis into a catheter for deployment as well as retrieval through either conventional trans-apical or trans-femoral delivery techniques.

Turning to the positioning and fixation challenges, instability and migration are the most prominent obstacles given that the mitral valve is subjected to high and repetitive loads in a cardiac cycle, with a high transvalvular pressure gradient that is near zero at diastole and can rise to 120 mmHg or more during systole and higher than 150 mmHg of systolic pressure for patients with aortic stenosis and systemic hypertension. The lack of calcium distribution at the mitral annulus also affects device stability and anchoring. Further, the transcatheter mitral valve replacement can be easily dislodged as the heart moves during each beating cycle.

With respect to sealing and paravalvular leakage, since the mitral valve annulus is large, a good fit between the native annulus and the prosthesis that minimizes paravalvular leak is desirable. Typically, a prosthetic mitral valve may have a large over-hanging atrial portion or flare which can prevent leakage, but, problematically, it also requires a large valve size at the ventricular level so that the prosthesis can be tightly fitted in the native mitral valve. Conventionally, a prosthetic mitral valve is smaller than the diseased native valve and additional material is added around the prosthetic valve to compensate for the large native mitral annulus. Undesirably, adding more material to a prosthetic valve increases the size of the delivery system.

Finally, with respect to the preservation of hemodynamic function, the operative positioning of a prosthetic mitral valve, which is conventionally large as described above, should not obstruct the LVOT at the anterior portion of the mitral annulus and should not interfere with the associated structures of a native mitral valve.

Accordingly, it would be beneficial to have a heart valve leaflet replacement system that does not suffer from the shortcomings and deficiencies of conventional valve prosthetics. It is desirable to secure the prosthetic mitral valve replacement system to the native mitral annulus. It is also desirable to improve positioning of a mitral prosthesis and prevent leaking of blood between the mitral prosthesis and the native mitral valve. Similarly, it is desirable to prevent further dilation of the native mitral annulus. Furthermore, other desirable features and characteristics will become apparent from the subsequent detailed description and the appended claims, taken in conjunction with the accompanying drawings and the foregoing technical field and background.

SUMMARY

Described herein is a heart valve leaflet replacement system and a method of securing a heart valve leaflet replacement system to one of the native valve annuli. It is contemplated that the method of securing a heart valve leaflet replacement system to one of the native valve annuli is configured to prevent dislodgment of the leaflet replacement system from the annulus and to ensure the proper coaptation between the implanted prosthetic leaflets with the remaining native leaflets. It is contemplated that the valve leaflet replacement device can be implanted via an open surgical procedure or transluminally via catheter. In one aspect, the heart valve leaflet replacement system can be configured to secure the prosthetic mitral valve to the native mitral annulus. In a further aspect, the associated methods can be configured to implant the replacement valve prosthesis and to help prevent further dilation of the native mitral annulus. For clarity, it will be appreciated that this disclosure will focus on the treatment of functional mitral regurgitation, however it is contemplated that the heart valve leaflet replacement system and the associated methods can be used or otherwise configured to be used to treat other valve disease conditions and replace other valves of the human heart, or could be used or otherwise configured to be used in other mammals suffering from valve deficiencies as well.

In one aspect, the heart valve leaflet replacement system can comprise a replacement prosthetic mitral valve that is configurable or otherwise sizable to be crimped down to fit within a delivery sheath and to subsequently be selectively expanded to an operative size and position once removed from the delivery sheath within the heart. In a further aspect, at least a portion of the prosthetic mitral valve can have a stent shape, which can comprise an upper flared atrial portion and a lower vertical ventricular portion. In one aspect, the upper flared portion can be configured to facilitate anchoring of the stent, which can help prevent paravalvular leakage and dislodgement of the stent. Further, the lower ventricular portion can displace a diseased native leaflet out of the blood flow tract and house at least one prosthetic leaflet. In another aspect, the prosthetic mitral valve can comprise a lining skirt that can be coupled to at least a portion of the inner and/or outer surfaces of the stent. In one exemplary aspect, at least one prosthetic leaflet can be mounted on the inner lumen of the stent and/or on at least a portion of the outer side of the stent, which can function in place of at least one native leaflet to restore normal valve function, e.g., to prevent mitral regurgitation.

In one aspect, at least one leaflet of the prosthetic mitral valve can have at least one prong-shaped structure which prevents the valve leaflets from billowing into the atrium and prolapsing. The at least one prong-shaped structure also acts to reduce prosthetic leaflet stress and facilitate the coaptation with at least one of the native mitral valve leaflets, in order to recreate the competent closure anatomy of a native mitral valve with sufficient leaflet coaptation length and height and proper leaflet angles during systole.

In one aspect, the delivery of the prosthetic mitral valve can be conducted using several desired delivery access approaches, such as, for example and not meant to be limiting, a surgical approach, a trans-septal approach, a trans-atrial, or a trans-apical approach. In one exemplary aspect, the trans-septal approach can comprise creating an opening in the internal jugular or femoral vein for the subsequent minimally invasive delivery of portions of the heart valve leaflet replacement system through the superior vena cava, which flows into the right atrium of the heart. In this exemplary aspect, the access path of the trans-septal approach crosses the atrial septum of the heart, and once achieved, the components of the heart valve leaflet replacement system can operatively be positioned in the left atrium, the native mitral valve, and the left ventricle. In one aspect, it is contemplated that a main delivery catheter can be placed therein the access path to allow desired components of the heart valve leaflet replacement system to be operatively positioned in the left atrium without complications.

In one aspect, a plurality of fixation members can be operatively positioned and implanted at desired locations in the native annulus prior to the delivery of the replacement prosthetic valve. In this aspect, the fixation members can improve the subsequent positioning and anchoring of the replacement prosthetic valve. In a further aspect, the plurality of fixation members can help prevent leakage of blood between the operatively positioned prosthesis and the native mitral valve.

In an exemplary aspect, the fixation members can be an anchor, having proximal and distal portions. In a further aspect, each anchor can be operatively inserted and embedded into the annular tissue. In one aspect, the distal portion of the anchor can be fully embedded or partially embedded into the annular tissue. In one aspect, the distal portion can be connected to the proximal portion of the anchor. In this aspect, the distal portion of the anchor can be configured to receive a flexible component that acts as a bridge connecting the prosthetic valve to the anchor. In this aspect, the flexible component can be used as a means for precisely guiding and securely maneuvering the prosthetic mitral valve to the native mitral valve.

In a further aspect, the flexible component can be a tether that is configured so one end of the tether is attached to the proximal portion of the anchor and the other end of the tether can exit the body. Subsequently, the prosthetic mitral valve can be delivered over the tethers and positioned over the anchors such that the upper flared portion of the stent can be in close proximity to the anchors.

In one aspect, it is contemplated that a plurality of locking devices can be delivered through a plurality of tethers and positioned over the upper flared portion of the stent immediately following the delivery of the prosthetic valve. In this aspect, a portion of the tether connected to the proximal portion of the anchor, will pass through the upper flared portion of the prosthetic valve, and enter the locking device, which will engage the tether and fixate the stent in the operative position against the plurality of anchors. The portion of the tether exiting the locking device can be subsequently removed using a conventional suture-like cutting device.

Therefore, in this aspect, the delivery system for the prosthetic valve can comprise a main deflectable delivery catheter that can house and act as a delivery pathway for the valve catheter, an assembly for delivery of the plurality of anchors, and an assembly for delivery of the prosthetic mitral valve and plurality of locking devices.

In one aspect, the locking device can be a distinct structure from the stent and fixation members. In one exemplary aspect, the locking device can be configured as a tubular structure, which can clamp on to at least one tether using one or more tabs extending radially inwards from one side of the tubular structure and forming a tight contact against the opposite side of the tubular structure. The tethers can have inline male protrusions that are configured to increase friction and axial resistance to prevent tether slippage. In this aspect, the tubular locking device can be delivered and released using a locking delivery system.

The locking delivery system can comprise a lock supporting catheter and a lock delivery catheter. The lock supporting catheter can comprise stiff and flexible portions. In this aspect, the stiff portion can be configured to open one or more tabs, i.e. push the tabs towards the wall of the locking device to allow the tether to pass through thereby facilitating sliding of the locking device along the tether. It will be appreciated that the flexible portion of the lock supporting catheter allows the catheter to flex and bend easily which can facilitate delivery of the locking device at different locations around the annulus. In this aspect, the locking delivery catheter can be a flexible catheter, which can be conventionally operated to push the locking device off the stiff portion of the locking supporting catheter so that it can release the tabs and grab onto the tether within the tubular structure of the locking device to effectively lock it into place along the tether.

It is noted that a brief episode of rapid ventricular pacing (180-220 beats/min) is often performed during implantation of transcatheter heart valves to minimize transvalvular flow and thereby reduce the risk of valve embolization during the procedure. The amount of time used for rapid pacing is minimal, usually between 14-29 seconds to minimize risk to the patient. It is contemplated that the prosthetic mitral valve can be deployed and secured to the native mitral valve within 25 seconds of rapid pacing using the delivery system of the invention. Following the transcatheter deployment of a plurality of anchors attached to tethers, the delivery system provides for precise deployment of the replacement prosthetic mitral valve, simultaneous delivery of multiple locking devices and secured attachment of the locking devices to the replacement prosthetic mitral valve within 25 seconds, followed by easy removal of the trailing tethers.

In one aspect, simultaneous delivery of multiple locking devices can be achieved using a lock housing structure. In this aspect, the lock housing structure can be configured with multiple lumens to house multiple locks and locking catheters. In this aspect, it will be appreciated that the lock housing structure can also be configured to load the prosthetic mitral valve onto the valve catheter. When the prosthetic mitral valve device is crimped into a smaller size and loaded onto a valve delivery catheter, the lock housing structure is loaded closest to the tip of the upper flared portion of the replacement prosthetic mitral valve. A plurality of the locking devices and lock catheters can be loaded into the lock housing structure, located adjacently to the tip of the upper flared portion of the replacement prosthetic valve, which will allow the locking devices to be deployed immediately after the replacement prosthetic valve.

In one aspect, of the prosthetic mitral valve delivery, following deployment of anchors to the native annulus attached to one end of the tethers, the other end of the tethers still outside the body, can be passed through the upper flared portion of the stent and housed within the lock catheters, which are then loaded into the lock housing structure. In one aspect, housing of the tethers within the upper flared portion of the stent and the lock catheters can be easily achieved using the tether supporting catheter, which can be eventually removed from the body prior to the release of the replacement prosthetic valve.

In one optional aspect, the lock housing structure is coupled to the valve catheter to prevent rotation between the prosthetic valve replacement and the valve catheter. Additionally, the valve catheter can be configured such that it will not rotate as it is advanced towards the targeted implant location within the native mitral valve during delivery. One advantage of this non-rotational feature is that it prevents the tethers from being tangled within the main deflectable delivery catheter.

Retracting the valve catheter will release the replacement prosthetic valve. In this aspect, release of the distal end of the prosthetic valve replacement can be achieved transannularly. When the distal end of the prosthetic valve replacement is partially released, the entire valve catheter can be positioned across the valve annulus. A complete valve release can be performed during rapid pacing. The lock catheters will be released immediately following the release of the replacement prosthetic valve.

Release of the lock and lock catheters can be achieved by manipulating the two linking structures that are coupled to the lock housing structure and the main delivery system handle. In a further aspect, one linking structure enables simultaneous push out of the locking catheters, and the second linking structure, adjacent to the first linking structure, enables release of the locking devices onto the upper flared portion of the replacement prosthetic mitral valve.

It is contemplated that any suture-like cutting device can be used to cut the remaining tethers exiting the proximal portion of the locking device. The entire delivery system can be removed, and the septal closing device can be used to close up the hole on the atrial septum.

Various implementations described in the present disclosure can include additional systems, methods, features, and advantages, which can not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

DESCRIPTION OF THE FIGURES

The features and components of the following figures are illustrated to emphasize the general principles of the present disclosure. Corresponding features and components throughout the figures can be designated by matching reference characters for the sake of consistency and clarity.

FIGS. 7A-7C are perspective views of exemplary stent designs with additional features to capture native leaflets. As exemplarily shown, the distal ventricular portion of the stent can have hooks, barbs, cables, and the like that extend radially to grab the surrounding native leaflets. The capturing components can be evenly distributed along the circumference of the lower ventricular portion of the stent, or only along the middle section of the lower ventricular portion of the stent, or only at the two ends of the lower ventricular portion of the stent.

FIGS. 8A-8E shows perspective views of exemplary stent designs with variable height and design along the stent circumference. As exemplarily shown in FIGS. 8A-8B, the bottom ventricular portion of the stent can have a meshed structure, or optionally as shown in FIGS. 8C-8E, the bottom ventricular portion of the stent can have a non-meshed structure. Further, the bottom ventricular portion can be selectively configured to attach and support the at least one prosthetic leaflet as exemplary shown in FIGS. 8C-8E.

FIGS. 10A'-10C''' are top elevational views of exemplary aspects of a prosthetic leaflet. FIGS. 10A'-10A''' shows prosthetic leaflets that have at least one additional tissue or leaflet coaptation extension that are configured to extend from the distal free-edge of each of the prosthetic leaflets (the side leaflets and the middle leaflets) and where exemplary aspects of the prong structures are configured to be operatively coupled to leaflet coaptation extension. FIGS. 10B'-10B''' is another exemplary aspect of the prosthetic leaflets in which there is no prong structure for the side leaflets, with only the middle leaflet having at least one prong structure. FIGS. 10C'-10C''' is another exemplary aspect of the prosthetic leaflets where the side leaflets are configured or slanted such that the portion of the side leaflets that are spaced away from the middle leaflet has a shorter leaflet height when compared to the portion of the side leaflets that are adjacent to the middle leaflet. In one aspect, the prosthetic leaflets of this example can optionally not have any prong structures.

FIGS. 11A and 11B show an exemplary aspect where the prosthetic heart valve replacement consists of two leaflets. FIGS. 11C-11H show an exemplary aspect where the prosthetic heart valve replacement consists of three leaflets. Illustrated in FIGS. 11C and 11D, the prosthetic leaflets can each have the same design. Optionally, illustrated in FIGS. 11E-11H, the prosthetic leaflets can have different designs. Further, the prosthetic leaflets can have a uniform height, or can have an extended free edge as illustrated in FIG. 11H to enhance coaptation, or can have a variable height as shown in FIGS. 11G and 11H.

FIG. 14A-14C are perspective views of computer generated models of a prosthetic heart valve leaflet replacement system, showing prosthetic leaflets coupled to an exemplary stent, where the leaflet and stent height is shorter at the sides.

FIGS. 18A-18C are perspective views of an exemplary anchor delivery system. In this aspect, the anchor delivery catheter tip in FIG. 18A can be coupled to the end of the anchor delivery catheter shown in FIG. 18C. The inner wall of the anchor delivery catheter tip can be configured to have two pins for engaging and holding the anchor in place as shown in FIG. 18B. In this aspect, the tether can be looped through the through slot on the atrial side of the anchor.

FIG. 27A shows the anchor being positioned at a desired installation point on the mitral annulus. FIG. 27B shows the anchor delivery member being rotated in a first direction to fixate the anchor into the mitral annulus. FIG. 27C shows the anchor delivery member being rotated in the opposite direction to detach the implanted anchor from the anchor delivery member.

FIG. 28A shows one configuration of a locking device with two tabs that are configured in series and bend inwards to push the tether against the inner wall of the locking device, thereby securing the locking device in place and preventing it from sliding along the tether. FIG. 28B shows a tether with inline male protrusions to facilitate locking of the tether to the locking device. FIG. 28C shows another configuration of the locking device where the two side walls are straight and at least one tab bends inwards against one side wall. FIG. 28D shows another configuration of the locking device with two tabs, each on each side wall and the two tabs meet at the center of the locking device where it will press against the tether to lock it in place.

FIG. 32A is a perspective view of an exemplary lock housing structure with four holes to house four tethers. FIG. 32B is a perspective view of the crimped prosthetic device located within the delivery catheter, four tethers are looped through the holes on the upper flared portion of the prosthetic device, and the locking structure resides adjacent to the tip of the upper flared portion of the prosthetic device.

FIG. 33A is a perspective view of the lock housing structure, showing five lumens, a central slot for attachment to the main delivery system, four side slots at the distal tip for engaging and pulling the eyelets of the prosthetic device into the valve catheter. FIG. 33B is a cross-sectional view of the tip of the lock housing structure.

FIGS. 45A-45B are schematic views of the stent being simultaneously operatively coupled to a plurality of anchors using a locking device delivery catheter. FIG. 45A illustrates one exemplary aspect of four locking devices being delivered at four locations on top of the flare portion of the stent via four tethers.

FIG. 48A was taken during valve opening with no pressure, wherein the flared portion of the device was positioned on top of the mitral annulus and fixated by sutures and the ventricular portion (not shown) was inside the left ventricle. FIG. 48B was taken during valve closure with a pressure about 120 mmHg. The prosthetic leaflets (P1, P2, and P3) can provide a surface for proper coaptation (i.e., visual a coaptation line) with the native leaflets.

FIG. 49A was taken during the release of the valve from the valve catheter, while five anchors were pre-attached to the mitral annulus. FIG. 49B was taken after the release of the valve prototype.

FIG. 50A was taken during the simultaneous release of the lock catheters. FIG. 50B was taken after release of the lock devices, and a pressure of 90 mmHg was applied, showing that the valve is securely anchored to the mitral annulus.

FIGS. 51A-51D are computed tomography images of the heart valve leaflet replacement system after being surgically implanted in the native mitral position of a porcine model. The images were taken during the systolic phase of a cardiac cycle. FIG. 51A shows the top view of the valve from the left atrium, showing all three prosthetic leaflets (P1, P2, and P3) coapting with the native anterior leaflet, the dark lines are the coaptation lines and the bright lines represent the stent frame. FIG. 51B is another view of the device, showing the prosthetic leaflet (P2) was coapting well with the native anterior leaflet (the arrow indicates the coaptation). FIG. 51C shows that the prosthetic leaflet (P1) was coapting well with the native anterior leaflet (the arrow indicates the coaptation). FIG. 51D shows the prosthetic leaflet (P3) is coapting well with the native anterior leaflet (the arrow indicates the coaptation).

FIG. 52 is echocardiogram of the implanted prosthesis inside the native mitral valve during systole. The dynamic motion of the native leaflet remains unperturbed after the implantation of the heart valve replacement system. The leaflet can coapt well with the prosthetic leaflets during systole.

FIGS. 53A-53F are a series of angiograms during the cardiac cycle showing the heart valve replacement system after being surgically implanted in the native mitral valve position of a porcine model. From these images, it is shown that the prosthetic leaflets of the device coapt well with the anterior leaflet of the native mitral valve, where there is none to trace regurgitation during left ventricular contraction. The data was obtained at 30-day follow up after the implantation.

DETAILED DESCRIPTION

Figure 1:
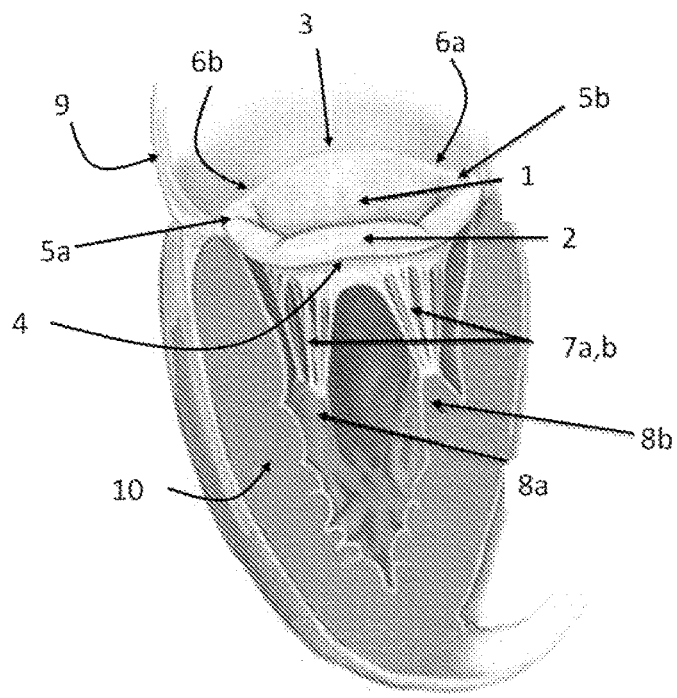
FIG. 1 is a perspective view of the anatomy of a native mitral valve, showing the location of the mitral valve (MV) in the heart.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features.

Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

For clarity, it will be appreciated that this disclosure will focus on the treatment of functional mitral regurgitation, however it is contemplated that the heart valve leaflet replacement system and the associated methods can be used or otherwise configured to be used to treat other types of mitral regurgitation or to replace other diseased valves of the human heart, such as tricuspid valve, or could be used or otherwise configured to be used in other mammals suffering from valve deficiencies as well.

As used throughout, the singular forms "a," "an" and "the" include plural referents unless the context clearly dictates otherwise. Thus, for example, reference to "a leaflet" can include two or more such leaflets unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance can or cannot occur, and that the description includes instances where said event or circumstance occurs and instances where it does not.

The word "or" as used herein means any one member of a particular list and also includes any combination of members of that list. Further, one should note that conditional language, such as, among others, "can," "could," "might," or "may," unless specifically stated otherwise, or otherwise understood within the context as used, is generally intended to convey that certain aspects include, while other aspects do not include, certain features, elements and/or steps. Thus, such conditional language is not generally intended to imply that features, elements and/or steps are in any way required for one or more particular aspects or that one or more particular aspects necessarily include logic for deciding, with or without user input or prompting, whether these features, elements and/or steps are included or are to be performed in any particular embodiment.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these cannot be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems can be understood more readily by reference to the following detailed description of preferred embodiments and the examples included therein and to the figures and their previous and following description.

Described herein is a heart valve leaflet replacement system and a method of securing a replacement prosthetic heart valve 12 to one of the native valve annuli. In one aspect, it is contemplated that the heart valve leaflet replacement system can be configured to secure a prosthetic mitral valve to the native mitral annulus. In a further aspect, the heart valve leaflet replacement system and the associated methods can be configured to alleviate mitral regurgitation during a patient's cardiac cycle and/or to help prevent further dilation of the native mitral annulus. It should be noted that it is contemplated that the heart valve leaflet replacement system 11 described herein can be used to replace any diseased valve within the heart. For illustrational purposes, the description in this invention will be focused on the mitral valve and the naming according to the mitral valve geometries. However, the designs described herein can be used in all other heart valves accordingly.

Referring to FIG. 1, the mitral valve 1 is located on the left side of the heart, between the left atrium 9 and left ventricle 10 and has anterior 1 and posterior 2 leaflets that are encompassed by the mitral annulus. In this aspect, the mitral annulus further has a fibrous portion 3, or fibrosa, which runs from the right trigone 6a to the left trigone 6b and is in continuity with a portion of the aortic valve and the posterior muscular portion 4. Further, chordae tendineae 7a,b originate from the respective major papillary muscles 8a,b of the left ventricular wall and connect to the respective mitral leaflets.

In one aspect, the heart valve leaflet replacement system 11 can comprise the replacement prosthetic mitral valve 12 and a transcatheter delivery system. In this aspect, and referring to FIG. 2, disclosed herein an exemplary aspect of a heart valve leaflet replacement system 11, showing the components and the fabricated prosthetic mitral valve 12. In this aspect, the prosthetic mitral valve 12 can be configured to be selectively compressed or otherwise constrained to a compressed position and loaded onto the delivery catheter.

The prosthetic mitral valve 12 can comprise a crescent shaped stent 31, at least one mobile prosthetic leaflet 16, and at least one prong structure 18 operatively coupling a portion of the prosthetic leaflet to the lower ventricular portion of the stent 14.

Figures 2A, 2B:
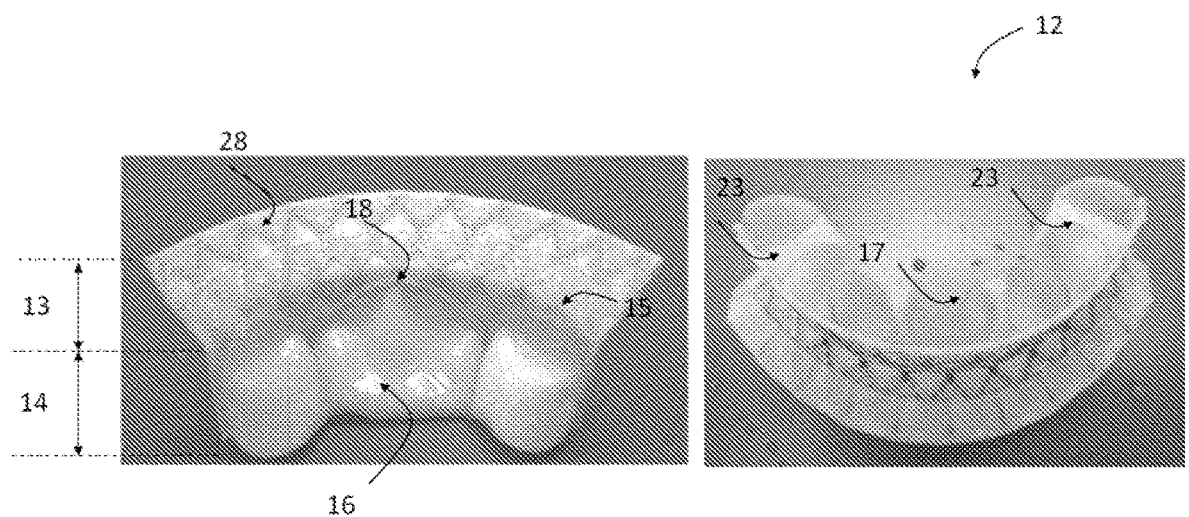
FIGS. 2A and 2B are perspective views of an exemplary aspect of a heart valve leaflet replacement system, showing a stent having an upper flared portion and a lower ventricular portion, a prosthetic pronged leaflet, where the prong couples the prosthetic leaflet to the lower ventricular portion of the stent.

In one aspect, the crescent shaped stent 31 of the replacement prosthetic mitral valve 12, as referring to FIGS. 2A-2B, can comprise an upper flared portion 13 and a lower ventricular portion 14. At least a portion of the upper flared portion 13 and/or a portion of the lower ventricular portion 14 can be formed to be self-expandable or balloon expandable to the desired operative position. In this aspect, it is contemplated that the stent 31 can be conventionally laser cut or woven into a desired stent design that can be radially collapsible and expandable. Thus, it is further contemplated that the stent can comprise a plurality of operatively linked components to form an expandable meshed or non-meshed body that can be made of a metal, including but not limited to, cobalt chromium, stainless steel; or a metal having inherent shape memory properties, including but not limited to, Nitinol. Optionally, it is contemplated that the stent can comprise a plurality of vertical stiff structures that are connected by soft materials such as biological tissue, synthetic materials such as polymers and the like. The stent can be configured to permit the natural dynamic motion of any remaining native leaflet(s) to coapt with the prosthetic leaflet(s).

In one aspect, it is contemplated that, in the expanded configuration, the inner surface of the stent 31 can define a substantially circular cross-sectional profile. It is further contemplated that the stent 31 can be configured to deform such that the inner surface of the stent defines a non-circular cross-sectional profile, including but not limited to, an elliptical cross-sectional profile or an asymmetric cross-sectional profile. As used herein, the term "asymmetric cross-sectional profile" includes any non-circular cross-sectional shape.

Figure 3:
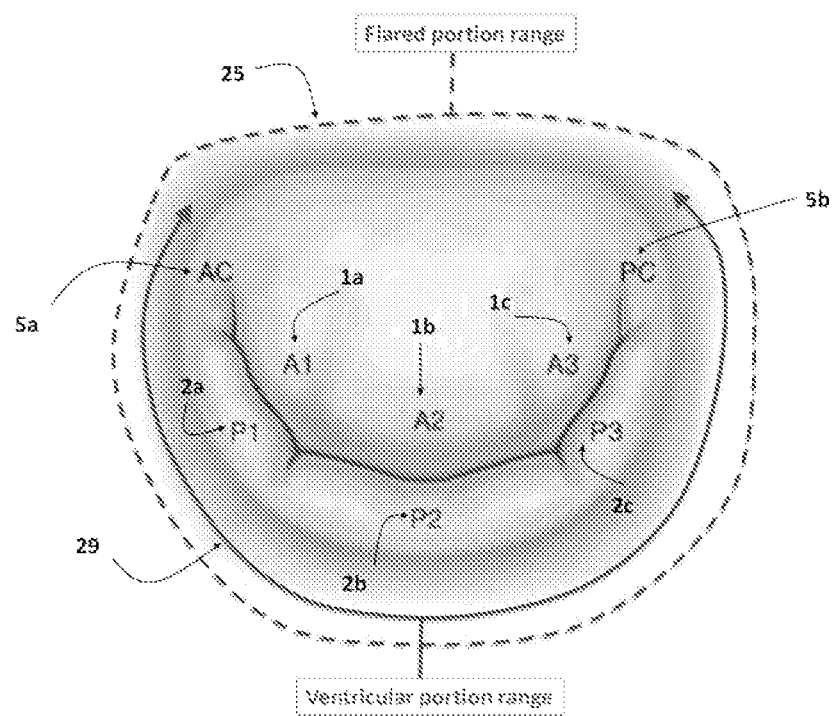
FIG. 3 demonstrates the circumferential dimensions of the device. The anterior mitral leaflet is divided into three scallops: A1, A2 and A3. The posterior mitral leaflet is divided into three scallops: P1, P2 and P3. The flared portion of the device can span the two commissures, AC-anterior commissure and PC-posterior commissure, or can cover the entire circumference of the mitral valve when operatively positioned. The ventricular portion of the device can span the two commissures, covering the entire posterior portion of the mitral valve.

In one aspect, as referring to FIG. 3, when implanted, it is contemplated that the upper flared portion 13 of the stent 31 can be configured to be positioned on and/or above the native annulus. In this aspect, the upper flared portion 13 of the stent 31 can be configured to facilitate anchoring, fixating, and sealing of the stent, which can assist in preventing paravalvular leakage and dislodgement of the stent post implantation. The mitral valve annulus is asymmetrical, which is illustrated in FIG. 3. The upper flared portion 13 of the prosthetic mitral valve 12 will cover or overlay the posterior portion of the mitral annulus, which is divided into three scallops: namely P1, P2 and P3. In one aspect, the upper flared portion 13 can span the two commissures, i.e., the AC-anterior commissure and the PC-posterior commissure. In another aspect, the upper flared portion 13 can cover the entire circumference of the mitral valve when operatively positioned.

In one aspect, at least a portion of the lower ventricular portion 14 can be positioned in the ventricular chamber of the heart and/or in contact with a portion of at least one native mitral leaflet.

Figure 4:
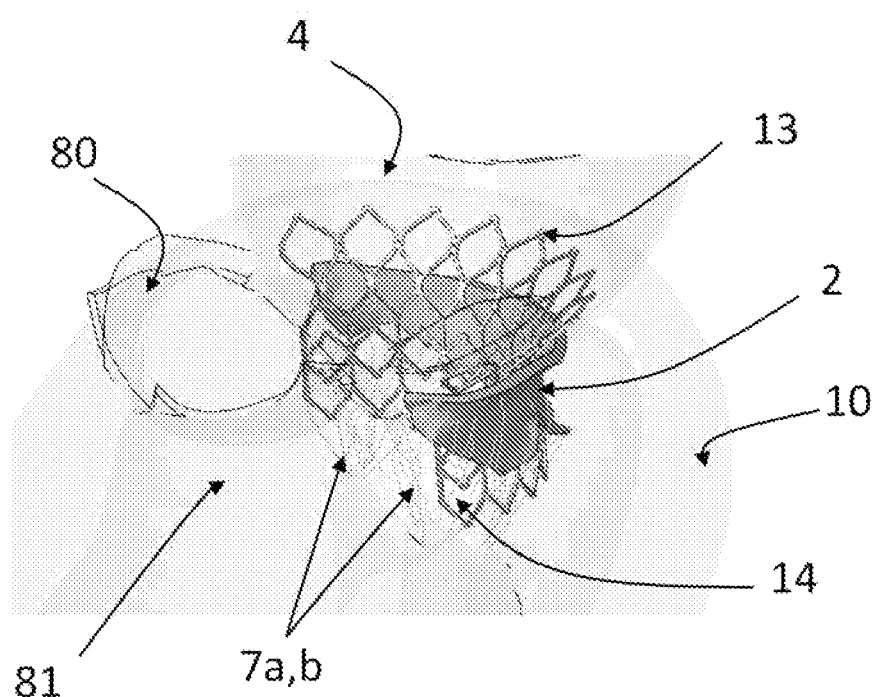
FIG. 4 is perspective view of the computer generated model of the prosthetic device, showing the upper flared portion and the lower ventricular portion of the stent of FIG. 2 without a skirt attached for clarity, shown in an exemplary operative position in the native mitral annulus in contact with the computer generated heart model.

FIG. 4 shows the computer generated stent 31 of the prosthetic mitral valve 12 being overlaid with a computer model of the partial heart, comprising the aortic annulus 80, the partial left ventricle 10, the papillary muscles 8, the left atrium 9, and the chordae tendineae 7. Those skilled in the art will appreciate that the partial circumference frame 31 in this invention, as shown in FIG. 4, can help prevent left ventricular outflow tract 81 obstruction (LVOTO). One potential advantage of the partial circumference structure of the lower ventricular portion 14 of the stent is that the stent frame does not interfere with the anterior mitral leaflet 1 when operatively positioned. The native leaflet is not constrained by the stent and can move freely, thereby reducing the risk of LVOTO. The lower ventricular portion 14 of the stent is configured to allow unperturbed motion of the native anterior leaflet.

In one exemplary aspect, the lower ventricular portion 14 of the stent can have a partial cylindrical or conical shape, and, optionally, can have a height range of between about 0.5 to about 1.5 times the radial length of the displaced diseased native leaflet(s). The lower ventricular portion 14 of the stent 31 can be configured to cover or overlie only select portions of the native posterior annulus circumference, and as a result of the expandable nature of the stent, can displace diseased native leaflet(s) out of the blood flow tract upon expansion to an operative position. Since the lower ventricular portion 14 can be configured to overlie select portions of the native annulus circumference and not the entirety of the native annulus circumference, this "open" configuration allows for the dynamic motion of the remaining native leaflet(s), e.g., the anterior mitral leaflet and for coaptation with the prosthetic leaflet(s). In one aspect, the outer diameter of the upper flared portion can be between about 5 to 15 mm larger than the inner diameter of the lower ventricular portion when the stent is expanded to the operative position.

In a further aspect, the lower ventricular portion 14 of the stent can extend radially from the anterior commissure 5a to the posterior commissure 5b, as exemplified in FIG. 3. In a further aspect, as exemplified in FIG. 3, the lower ventricular portion 14 of the stent can have a "C"-shaped cross-section where one lateral edge 26b lands at the cleft between the anterior leaflet and anterolateral commissure leaflet and the other lateral edge 26a lands at the cleft between the anterior leaflet and the posteromedial commissure leaflet.

Figure 5A:
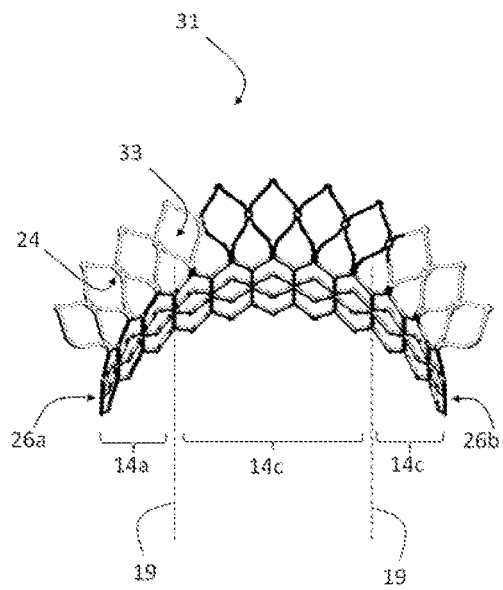
FIGS. 5A and 5B are perspective views of one exemplary aspect of the stent which consists of a plurality of cell structures and the junctions between adjacent cells, showing the upper flared portion, the lower ventricular portion, and the portions housing each of the prosthetic leaflets. In one aspect, it is contemplated that in the upper flared portion, the junctions or anchor openings can form bores that are configured to facilitate delivery of the stent into the mitral position via tether components. In one exemplary aspect, the bores can have a substantially circular shape.

In one aspect, as shown in FIG. 5A, openings 24 defined in the upper flared portion 13 of the stent 31 can have a circular, square, diamond, triangle, or asymmetrical shapes. The area of the openings 24 of the upper flared portion 13 can have an area range from about 0.2 mm² to 2 mm².

Figure 5B:
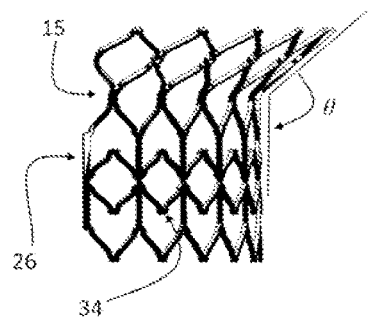
Figure 6A:
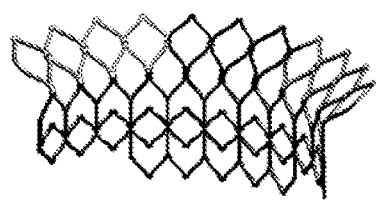
FIGS. 6A-6E are perspective views of exemplary stent designs. As exemplarily shown, the heights of the lower ventricular portion of the stent can vary, particularly on the two lateral ends. Optionally, the cell structures of the lower ventricular portion of the stent can be of different shapes and dimensions.
Figure 6B:
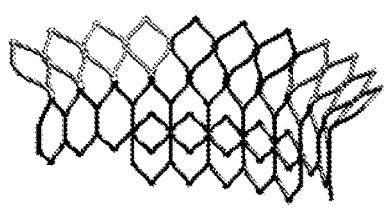
Figure 6C:
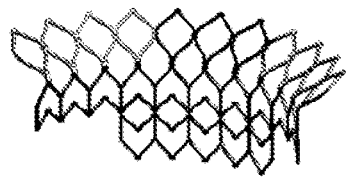
Figure 6D:
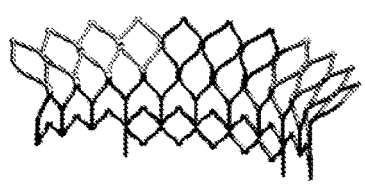
Figure 6E:
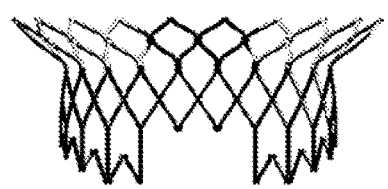

In one aspect, as shown in FIG. 5B, the angle between the upper flared portion 13 and the lower ventricular portion 14 of the stent can vary between 90 and 150 degrees, such that the stent frame can conform to the native curvature of the left atrium.

In one aspect, as shown in FIGS. 6A-6E, it is contemplated that the height of the lower ventricular portion 14 of the stent can vary along the covered annulus circumference. Optionally, the height of the lower ventricular portion 14 of the stent that covers the middle part 14b of the posterior mitral leaflet can be substantially longer than, or the same height as the lower ventricular portion 14 of the stent that covers the two lateral parts of the posterior mitral leaflet 14a,c, as shown in FIG. 5A. It is contemplated that the lower ventricular portion 14 of the stent that covers the two lateral parts of the posterior mitral leaflet 14a,c can be shorter in the axial direction such that it does not interfere with native anterior leaflet, chords, and left ventricle when operatively positioned.

In one aspect, as shown in FIG. 8C, the lower ventricular portion 14 of the stent can be formed with at least one vertical member or elongated strut 85 that extends from at least one location on the upper flared portion 13 of the stent 31. Optionally, this elongated strut 85 can be a straight or a curved segment extended axially, as exemplified in FIG. 8D. In a further aspect, the elongated strut 85 can branch out to form a secondary strut to facilitate sewing of the linking skirt or leaflet materials. It is contemplated that the elongated strut can be shaped as that of the leaflet attachment edge, as exemplified in FIG. 8E.

As shown in FIGS. 7A-7C, the bottom 27 of the ventricular portion of the stent can be configured with features such as flanges, hooks, coils, clips, 32 that are configured to capture the native leaflets when operatively positioned. In this aspect, the device can be further fixated and anchored to the native valve. This capturing mechanism can also further enable pannus formation that acts as sealing agent and prevents paravalvular leakage. In one aspect, as exemplified in FIG. 7A, upon deployment, at least three hook-like components 32 can extend radially from the stent strut and grab the native leaflets and chords. In one aspect, as exemplified in FIG. 7B, upon deployment, the hook-like components 32 can extend only from the middle part of the stent 14b. In another aspect, as exemplified in FIG. 7C, upon deployment, the hook-like components 32 can extend only from the lateral parts 14a,c of the lower ventricular portion 14 of the stent 31.

In an expanded position, as exemplarily shown in FIGS. 5-9, the lower ventricular portion 14 of the stent 31 can have an outer diameter ranging from about 20 mm to about 60 mm, and more preferably, from about 30 mm to about 50 mm. In a particular exemplary aspect, and without limitation, the lower ventricular portion 14 of the stent 31 can have an outer diameter of about 36 mm. However, it is contemplated that the lower ventricular portion 14 of the stent 31 can have any operative outer diameter that permits proper positioning of the stent within the selected channel of the heart of the subject.

It is contemplated that the diameter of the stent 31, the spacing between parallel struts and/or adjacent openings within the mesh pattern of the stent, and the mechanical properties of the stent can be selectively varied as necessary to achieve a desired position and/or desired performance characteristics within the selected chamber of the heart of the subject. In exemplary aspects, the spacing between parallel struts and/or the dimensions of adjacent openings within the mesh pattern of the stent 31 can be non-uniform throughout the stent 31. It is further contemplated that the stent 31 can be configured for deformation to an elliptical shape. It is still further contemplated that the mesh configuration of the stent 31 can provide sufficient structural integrity to prevent collapse of the stent upon exposure to compressive loading during valve closure, including but not limited to, mitral valve closure. In addition, the stent 31 can be configured to accommodate and tolerate sufficient radial expansion force to permit secure positioning of the stent on the mitral annulus within the heart of the subject.

Figure 9A:
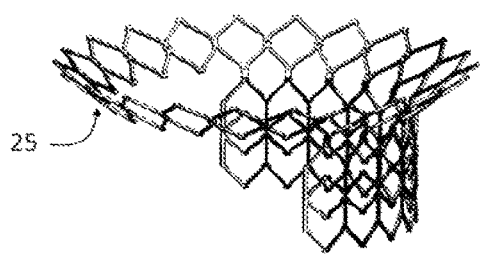
FIGS. 9A and 9B are perspective views of an exemplary aspect of the stent where the upper flared portion covers the entire native mitral annulus, and a perspective view of the stent in the operative position.
Figure 9B:
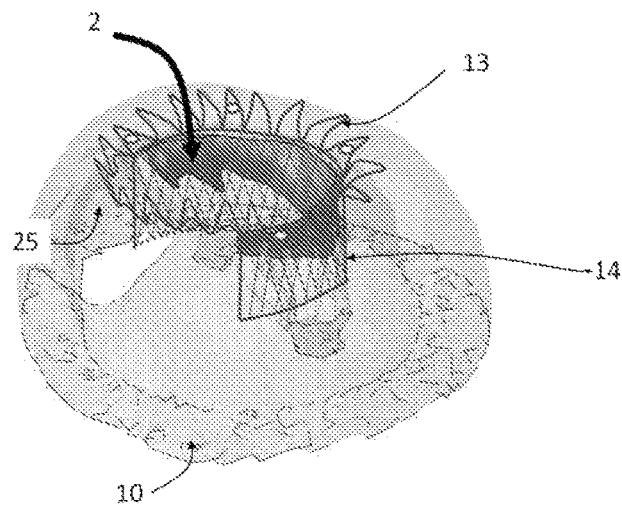
Figure 11A:
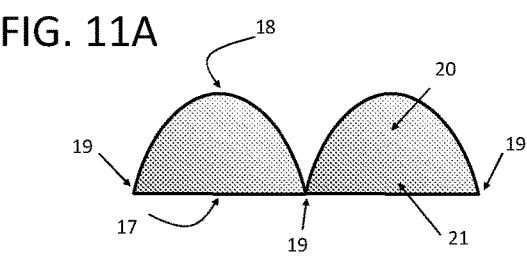
FIGS. 11A-11H are top elevational views of different exemplary aspects of the prosthetic leaflet structures including belly region, free edge, and commissure regions.
Figure 11B:
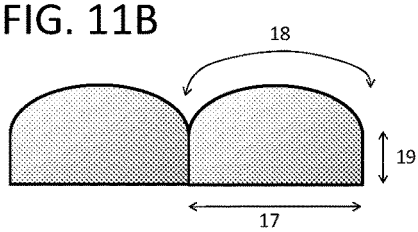
Figure 11C:
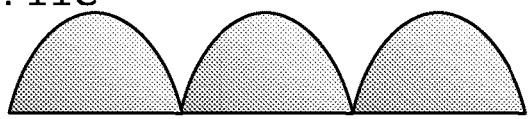
Figure 11D:
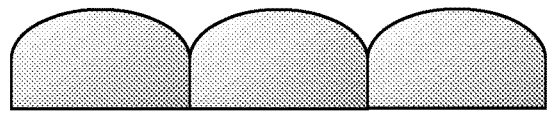
Figure 11E:
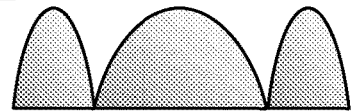
Figure 11F:
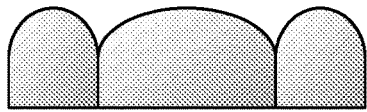
Figure 11G:
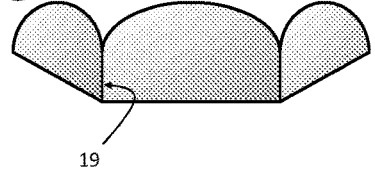
Figure 11H:
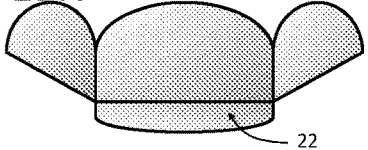
Figure 12A:
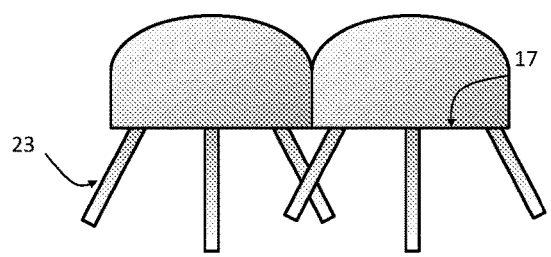
FIGS. 12A-12F are top elevational views of exemplary aspects of the coaptation and strength enhancing prong structures coupled to portions of a prosthetic leaflet, showing a plurality of prong structures operatively coupled to a distal free-edge, to a portion of a coaptation region, and/or to a belly region of the respective prosthetic leaflet.
Figure 12B:
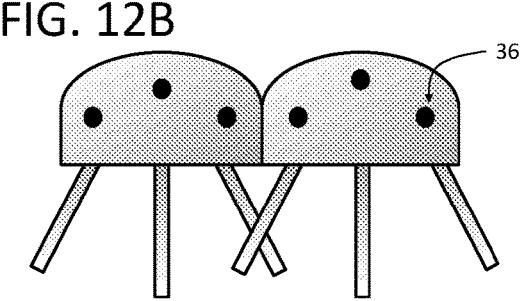
Figure 12C:
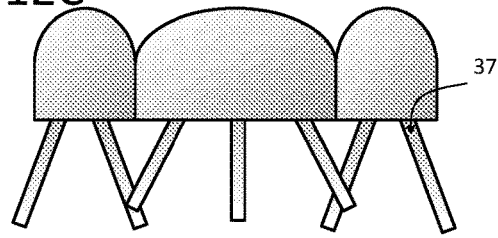
Figure 12D:
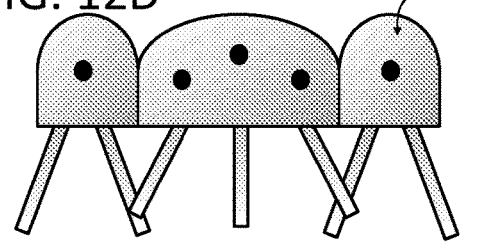
Figure 12E:
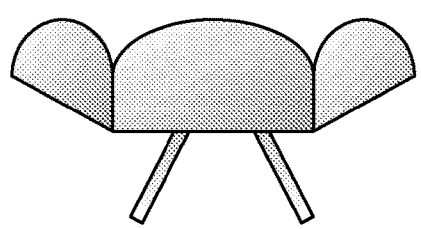
Figure 12F:
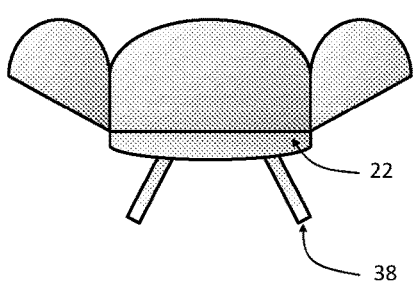

In one aspect, as exemplified in FIG. 9, it is contemplated that the lower ventricular portion 14 of the stent 31 can extend circumferentially less than 360 degrees, while the coupled upper flared portion 13 can be formed to extend circumferentially about 360 degrees.

In one aspect, the replacement prosthetic mitral valve 12, as shown in FIG. 2, can comprise a skirt 28 that can be coupled to at least a portion of the inner and outer surfaces of the stent. In one exemplary aspect, it is contemplated that the skirt 28 can be sewn to at least a portion of the inner and outer surfaces of the stent with non-absorbable sutures. In an exemplary aspect, the skirt 28 can be formed of biocompatible materials, for example but not limited to, biocompatible fabric, bovine, or porcine pericardium, and the like.

In one aspect, the at least one prosthetic leaflet 16 can be mounted on the inner surface of the stent. In one aspect, the at least one prosthetic leaflet 16 can be mounted on the inner surface of the lower ventricular portion 14 of the stent 31. It is contemplated that the prosthetic mitral valve 12 can comprise a plurality of prosthetic leaflets 16, in which all of the leaflets can have the same shape or in which one or more of the plurality of leaflets can have a different shape. In various aspects, each leaflet can comprise a free edge 17, two commissure attachment regions 19, an attachment edge 18, and respective coaptation 21 and belly regions 20.

In one aspect, the at least one prosthetic leaflet 16 can be configured to be mobile throughout the cardiac cycle such that the prosthetic leaflet 16 can coapt with at least one native leaflet during valve closure to prevent the regurgitation of blood through the valve. In one aspect, the prosthetic leaflets 16 can be flexible and mobile enough to contact with the native leaflet 1 without damaging the native leaflet, and can open fully during valve opening such that it does not to perturb normal blood flow through the valve or induce stenosis.

In one aspect, as exemplified in FIG. 10A, each prosthetic leaflet 16 can have additional extension tissues 22 on the free edge 17 that are configured to increase the coaptation zone between the prosthetic leaflets and the native anterior leaflet. In this aspect, it is contemplated that a plurality of prong structures 23 can be configured to be coupled to the coaptation enhancing extension tissues 22. The additional tissue 22 on the free edge 17 of each prosthetic leaflet 16 can be between about 1 to about 10 mm. In this aspect, the prong structures can be configured to shape the prosthetic leaflets into an optimal coaptation surface for the native anterior mitral leaflet when pressurized to ensure optimal coaptation and prevent prolapse and the leakage of blood through the valve.

In one aspect, as exemplified in FIGS. 10B and 10C, the prosthetic valve replacement can comprise three prosthetic leaflets 16: a middle leaflet 16b and two side leaflets 16a,c. The middle prosthetic leaflet 16b can have a plurality of prong structures 23 and the two side prosthetic leaflets 16a,c can be without prong structures 23. In another aspect, the height of the commissure attachment regions 19 of the prosthetic leaflets 16 can be the same or different. In a further optional aspect, as shown in FIG. 10C, the commissure attachment regions 19 of the two side prosthetic leaflets 16a,c can be shortened at the two lateral edges 26a,b of the lower ventricular portion 14 of the stent 31.

In one embodiment of the replacement prosthetic heart valve shown in FIG. 2, the two commissure leaflets 16a,c can span about 30°-60° of the stent circumference. In one exemplary aspect, the commissure leaflet 16a,c shown in FIG. 10A can have a maximum width of 15.0 to 30.0 mm and height of 10.0 to 20.0 mm, where the extended free edge portion is about 1.0 to 6.0 mm higher than the tip of the leaflet-stent attachments illustrated in FIGS. 15 and 16. In this aspect, the extended free edge can ensure sufficient coaptation between the prosthetic commissure leaflets 16 a,c and the native anterior mitral leaflet at A1 and A3 regions referring to FIG. 3 as well as the middle prosthetic leaflet 16b while keeping the overall stent height low to prevent device interference with the surrounding native structures, i.e. the papillary muscles and myocardium, when operatively positioned. Further in this aspect, the prong structure can have a length of 5.0 to 15.0 mm and act to stabilize the extended free edge and aid in proper coaptation between the sides of native anterior mitral leaflet and prosthetic commissure leaflets with a coaptation height of about 2.0 to 7.0 mm. The tip of the prong structure 23 can be configured to be at an angle of about 20° to facilitate attachment to the similarly angled stent strut and the prong stent attachment points shown in FIGS. 15 and 16. Referring to FIG. 10A, the middle prosthetic leaflet 16b can span about 60°-120° of the stent circumference. Preferentially, the middle leaflet 16b can be configured to span a larger circumference of the stent than the two side commissure leaflets 16a,c such that the prosthetic leaflets can better coapt with the native anterior mitral leaflet at the A2 region during valve closure. In one exemplary aspect, the middle prosthetic leaflet 16b can have a maximum width of 20.0 to 35.0 mm and height of 10.0 to 20.0 mm, where the extended free edge portion is about 1.0 to 7.0 mm higher than the tip of the leaflet-stent attachment points illustrated in FIGS. 15 and 16. In this aspect, the extended free edge can ensure sufficient coaptation between the middle prosthetic leaflet 16b and the adjacent prosthetic commissure leaflets 16a,c as well as the native anterior mitral leaflet at A2 with a coaptation height of about 4.0 to 7.0 mm while keeping the overall stent height low. Further in this aspect, the middle prosthetic leaflet 16b can be configured to have two prong structures extending from the extended free edge 22 with a length of 5.0 to 15.0 mm that can act to stabilize the extended free edge and aid in proper coaptation between the middle prosthetic leaflet 16b and native mitral anterior leaflet.

In one aspect, the at least one prosthetic leaflet 16 can be mounted on the inner surface of the upper flare portion 13 of the stent 31. Optionally, selective portions of the prosthetic leaflet 16 can be mounted on the outer surface of the stent 31, for example, the prosthetic leaflets can be wrapped around the sides of the stent 31 to act as a cushion between the stent 31 and native tissue when operatively positioned.

Referring to FIG. 11, the plurality of prosthetic leaflets 16 can be configured without prong structures 23 extending from the leaflet free edge 17. In one aspect, shown in FIGS. 11A and 11B, the prosthetic valve replacement can be configured with two identical leaflets. In another aspect shown in FIGS. 11O and 11D the prosthetic valve can be configured with three identical leaflets 16. Optionally, the commissure side leaflets 16a,c can be differ in shape to the middle leaflet 16b as shown in FIGS. 11E and 11F. Further in this aspect, the plurality of prosthetic leaflets can be configured to vary in the number of leaflets, size, height, and length, as shown in FIGS. 11G and 11H, to permit proper coaptation and opening.

Referring to FIG. 12, in one aspect, the prong structures 23 can be coupled to the leaflet free edge 17. In another exemplary aspect, the prong structures 23 can couple to the leaflet belly 20, or optionally to the extended free edge zone 22. It is contemplated that the prong structures 23 can be configured with a differing material to the prosthetic leaflet 16, for instance, but not limited to, biocompatible fabric, suture, or tissue, and can be attached to the prosthetic leaflet 16 in a number of ways, for instance by adhesive or suturing, to various regions on the prosthetic leaflet 16.

Figure 13A:
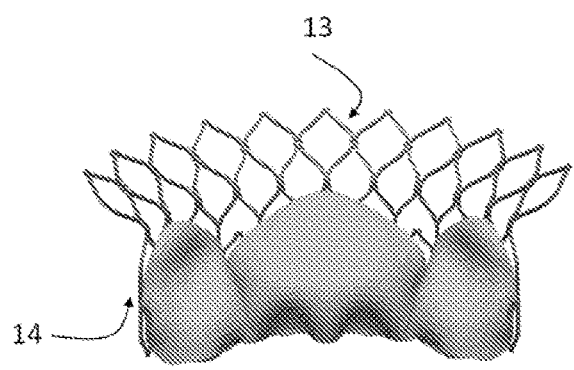
FIGS. 13A-13B are perspective views of computer generated models of a prosthetic heart valve leaflet replacement system, showing prosthetic leaflets coupled to an exemplary stent, where the leaflet and stent height is uniform along the device circumference.
Figure 13B:
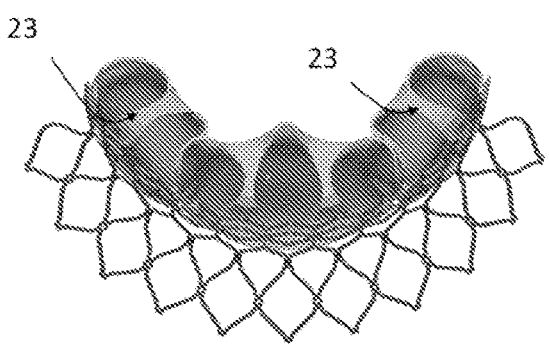

Referring to FIG. 13, in one aspect of the prosthetic valve replacement, the plurality of prosthetic leaflets 16 can be attached to the inner surface of the ventricular portion of the stent 14 along the leaflet attachment edges 18 as well as at the attachment tabs on the prong structures.

In another aspect, referring to FIG. 14, the plurality of prosthetic leaflets 16 can be configured without prong structures 23 and can be attached to the inner surface of the ventricular portion of the stent 14 along the leaflet attachment edges 18 only. Optionally, the commissure leaflets 16a,c can be shorter on the sides away from the center leaflet 16b corresponding to one aspect of the ventricular portion of the stent 14 where it is shorter on the sides.

Optionally, the at least one prosthetic leaflet 16 can have a shape similar to the native diseased valve the prosthetic valve 12 is intended to replace, or a different shape from those illustrated in FIG. 10 to FIG. 12, including, but not limited to, a square, rectangular, triangular, oval, circle, or other asymmetric shape.

Figure 15:
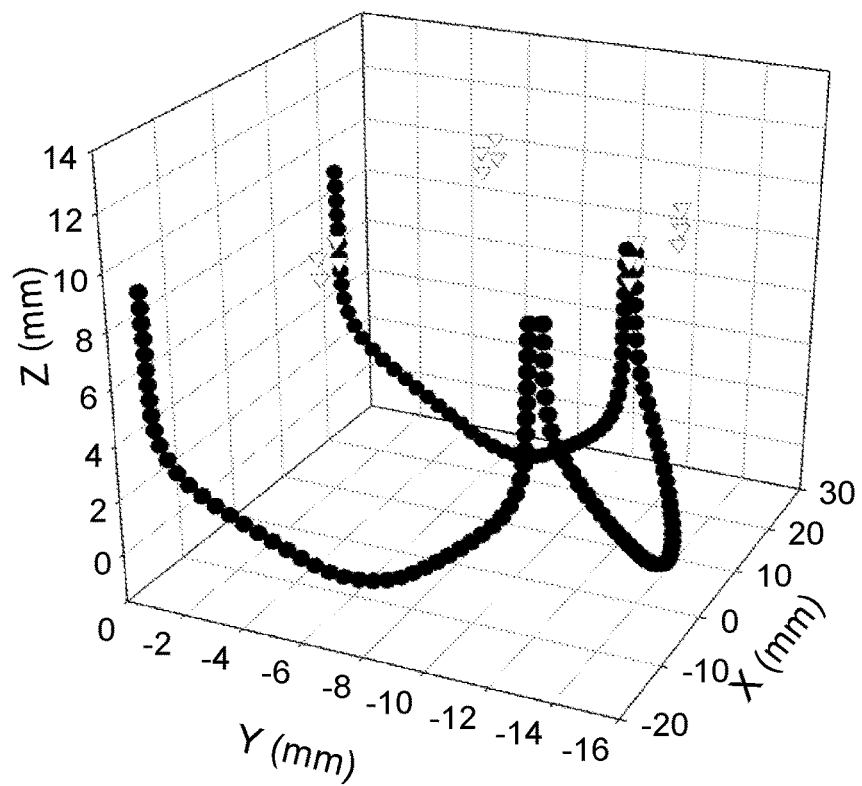
FIG. 15 illustrates the prosthetic leaflet to stent attachment points in three dimensional space for one exemplary aspect of a heart valve replacement system where the solid dots indicate the attachment points for the edges of the prosthetic leaflets and the open triangles indicate the attachment points of the prong structures to the stent.
Figure 16:
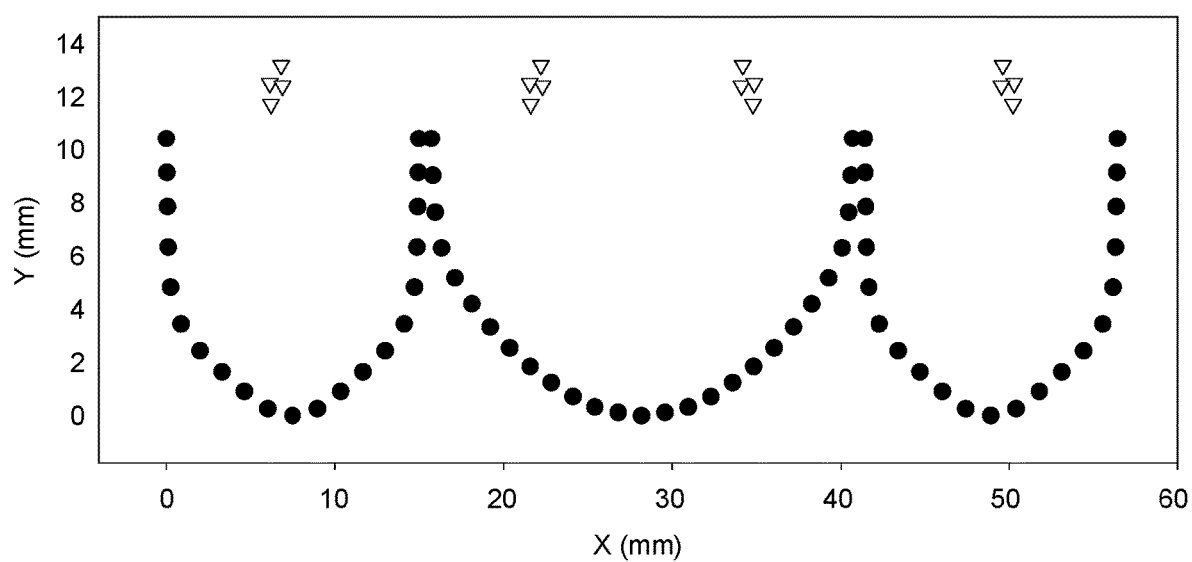
FIG. 16 illustrates the prosthetic leaflet to stent attachment points in two dimensional space for one exemplary aspect of a heart valve replacement system where the solid dots indicate the attachment points for the edges of the prosthetic leaflets and the open triangles indicate the attachment points of the prong structures to the stent.

In one exemplary aspect, the prosthetic leaflets can be configured to attach to the stent at a juncture defined by the two-dimensional and three dimensional leaflet-stent attachment curves shown in FIGS. 15-16, where the solid dots indicate the leaflet edge 18 attachment points, and the open triangles indicate the prong structure 23 attachments to the stent. This specific leaflet and prong stent attachment design and its variations (+/−25% derivation from the illustrated design curves) are optimized for optimal leaflet coaptation and well as leaflet stress reduction during the cardiac cycle while having a large effective orifice area without hitting the stent during valve opening. This design can be scaled, or proportionally adjusted, or un-proportionally adjusted for different sizes of the valve, provided these structures of the leaflet and prongs are used for the purpose of maintaining proper coaptation and reducing leaflet stress and increasing valve durability.

In one aspect, a means for guiding and anchoring the prosthetic valve 12 to the native annulus can comprise a plurality of fixation members coupled to flexible and elongated components. In one aspect, the fixation members can be anchors, hooks, or barbs that fixate into the annular tissues. The fixation members, for example, the anchor 30 can be sequentially delivered and implanted at the desired locations via a steerable catheter. In a further aspect, it is contemplated that a method of implanting anchors 30 can be implemented prior to the delivery of the prosthetic mitral valve 12. In another aspect, a plurality of anchors 30 can be configured to help prevent leakage of blood between the operatively positioned prosthetic valve 12 and the native mitral annulus. In another aspect, a plurality of anchors 30 can be configured to facilitate cinching of the diseased annulus in the circumferential direction to reduce the annular dimensions.

In another aspect, the plurality of anchors 30 can be directly attached to the stent. In this aspect, it is contemplated that the prosthetic valve 12 can be deployed simultaneously with the anchors 30, and the anchors 30 can be selectively configured to engage the native annulus once the prosthetic valve 12 is in the operative position to fixate the device on the native annulus.

In one aspect, as exemplified in FIGS. 17-21, each anchor 30 can comprise a distal portion 39, a proximal portion 40, and a tether portion 44. It is further contemplated that the distal portion 39 of each anchor 30 can be configured to implant into the native annulus tissue and to resist separation after implantation. In an exemplary aspect, the distal portion of each anchor 39 can have, but is not limited to, a spiral shape, a coil shape, a pronged shape, a screw shape, and a barbed hook shape. The anchors 30 can be formed of, but are not limited to, Nitinol, stainless steel, cobalt chromium, polymer, and the like.

Figure 17:
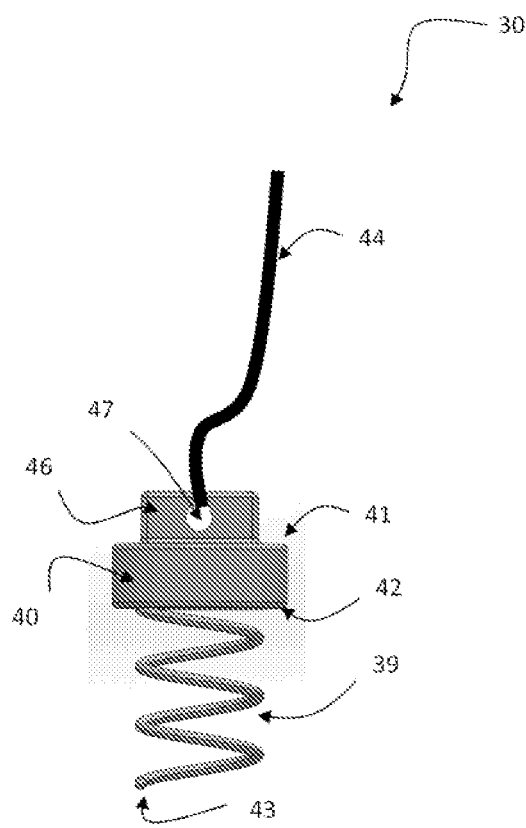
FIG. 17 is a side elevational view of an exemplary aspect of the anchor for the heart valve leaflet replacement system that is configured to be implanted, showing the atrial side of the anchor having a through slot configured to accept a tether, and two L-shape slots on two opposite sides configured for the anchor delivery member to engage for delivery, the ventricular side of the anchor that is configured for implantation, and anchor technical specifications.
Figure 19:
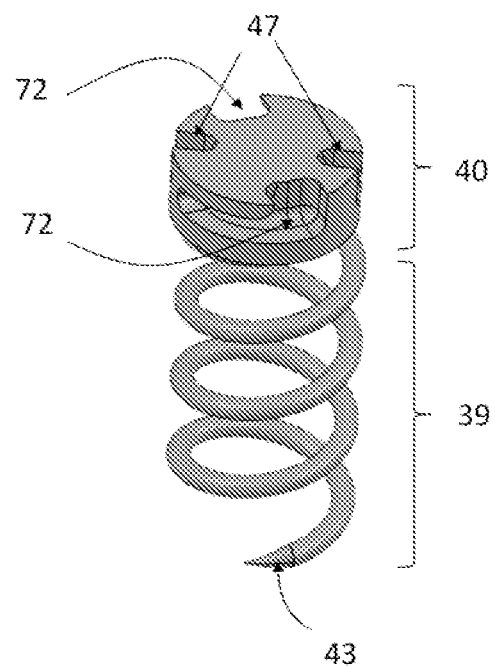
FIG. 19 is a perspective elevational view of an exemplary anchor delivery catheter for delivery of an anchor.

As one skilled in the art will appreciate, the anchors in this invention are specially configured to safely secure the prosthetic mitral valve 12 on the muscular annular section of the mitral valve. The anchor 30, as exemplified in FIG. 17, is configured to withstand the total force exerted to the prosthetic leaflet, without being pulled off the muscular portion of the annulus. Table 1 of FIG. 17 shows that the total force exerted to the prosthetic leaflet can be estimated by calculating the total area of prosthetic leaflet surface and the ventricular pressure. Table 1 displays two exemplary prosthetic valve sizes and the calculated forces exerted on the prosthetic leaflet. In one aspect, for an average size 29 mm diameter valve, assuming 140 mmHg of ventricular pressure, a total force of 12.33 N is required to secure the prosthetic mitral valve 12 in the native valve. Therefore, it is contemplated that the number of anchors to be used should be able to hold at least a total force of 12.33 N.

It is contemplated that each anchor configuration in this invention, as exemplified in FIGS. 17-24, can withstand at least 3 N, at least 4 N, or at least 5 N. In one aspect, one anchor can be placed at the right commissure (right trigone region of the mitral valve) and the other anchor can be placed at the left commissure (left trigone region of the mitral valve). It is contemplated that the height of the proximal portion 40 of the anchor 30 can be between about 1 and about 3 mm, and the length of the distal portion 39 of the anchor can be between about 3 and about 6 mm. In an exemplary aspect, as shown in FIGS. 17 to 21, the distal portion 39 can have a coiled shape with between about 3 to 6 coils. In this aspect, it is contemplated that the coiled distal portion 39 can have a wire diameter of 0.3 to 1 mm, and the formed outer diameter of the coiled distal portion 39 can be from about 2 to about 5 mm.

In one aspect, the tip 43 of the distal portion 39 of the anchor 30, as exemplified in FIG. 18, can comprise a tip that is shaped and configured to facilitate easy penetration into the annular tissue. In one exemplary aspect, the tip 43 of the distal portion 39 of the anchor 30 is curved to the same pitch as the distal portion 39 of the anchor 30. In another exemplary aspect, the tip 43 of the distal portion 39 of the anchor 30 can be straight. Optionally, the tip 43 of the distal portion 39 of the anchor 30 can have an arc length of from about 1 mm to 3 mm.

In another aspect, as shown in FIG. 18, the proximal portion 40 of the anchor 30 can define a slot 47 that is configured for attachment of a tether. It is contemplated that the tether 44 can be looped through the slot 47 on the proximal portion 40 of the anchor 30. Optionally, the proximal portion 40 of the anchor 30 can also define two L-shaped slots 72 that are configured to receive two pins 50 inside the anchor delivery catheter tip 49, as shown in FIG. 19A-19C. In this aspect, it is contemplated that the anchor 30 could be operatively implanted by rotating the anchor delivery catheter 48 in a first rotative direction. Further in this exemplary aspect and as one skilled in the art will appreciate, the anchor 30 can be subsequently separated from the anchor delivery catheter tip 49 by rotating the anchor delivery catheter 48 in a second rotative direction that is opposite to the first rotative direction to remove the pins 50 from the slots on the proximal portion of the anchor 30.

Figure 20:
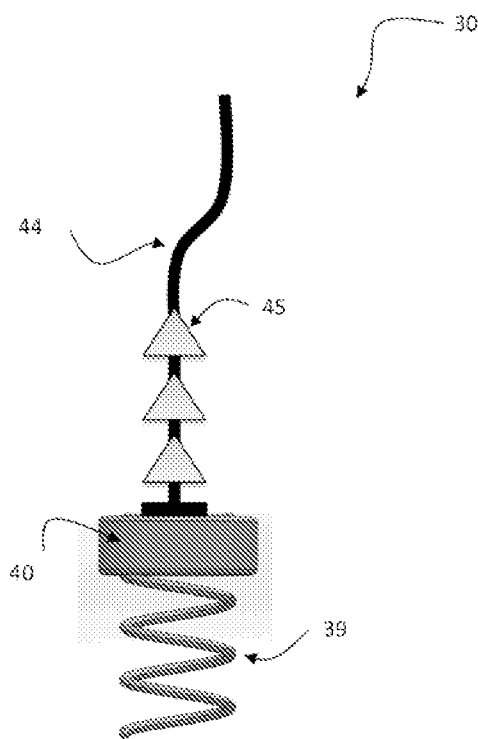
FIG. 20 is a side elevational view of an exemplary anchor for the heart valve leaflet replacement system that is configured to be implanted, showing a means for locking the stent to the anchor coupled to a portion of a tether portion that extends from the atrial side of the anchor and showing the ventricular side of the anchor that is configured for implantation.
Figure 21:
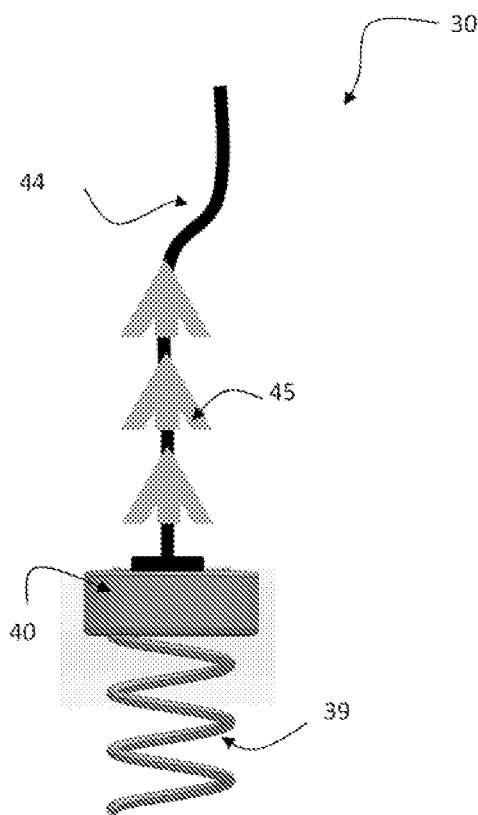
FIG. 21 is a side elevational view of an exemplary anchor for the heart valve leaflet replacement system that is configured to be implanted, showing a means for locking the stent to the anchor coupled to a portion of a tether portion that extends from the atrial side of the anchor and showing the ventricular side of the anchor that is configured for implantation.

As shown in FIGS. 20-21, it is contemplated that the means for locking the stent 31 to the anchors 30 can comprise at least one locking structure 45, including but not limited to, ridge engaging teeth, barbs, zip ties, pliable barb or key element, a cone shape, a square shape, an arrow shape, a circular shape, a triangular shape, a dome shape, and the like. It is contemplated that the locking structures 45 can be configured to allow passage of a portion of the upper flared portion 13 of the stent 31 down the tether portion 44 towards the left ventricle 10, and to resist the subsequent movement of the upper flared portion 13 of the stent 31 in the opposite direction. In another aspect, it is contemplated that the locking structures 45 can be configured in series along the tether portion 44 to allow for adjustment of the distance between the stent 31 and the anchor 30, and allow the stent 31 to be operatively locked even when there is a misalignment between the stent 31 and anchors 30. In an exemplary aspect, it is contemplated that the one or more locking structures 45 can be formed of, but are not limited to, polymers, polytetrafluoroethylene (PTFE), metallic materials, or a combination of these materials.

Figure 22:
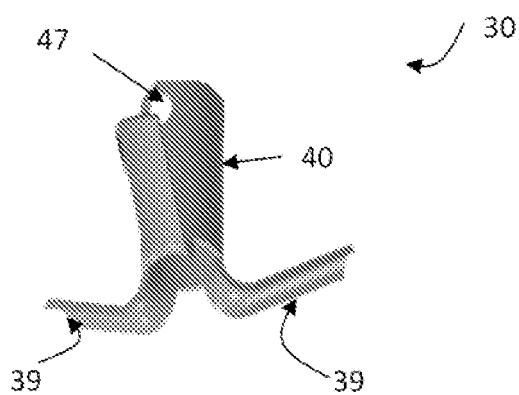
FIG. 22 is a perspective view of an exemplary anchor for the heart valve leaflet replacement system.
Figure 23:
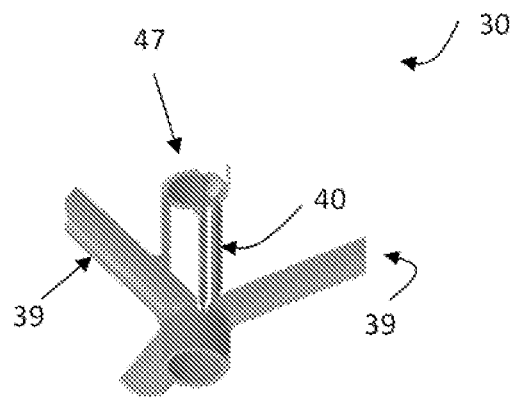
FIG. 23 is a perspective view of an exemplary anchor for the heart valve leaflet replacement system.
Figure 24:
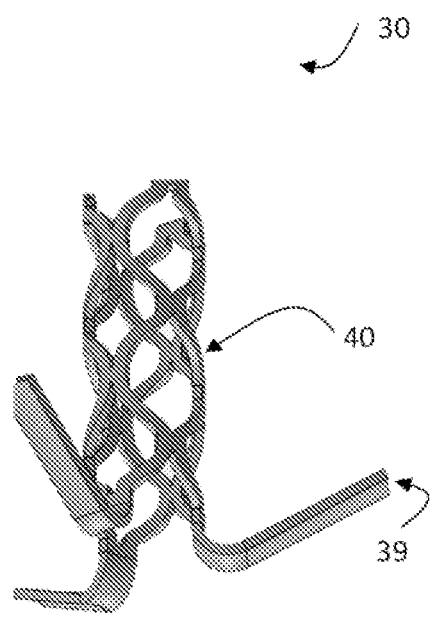
FIG. 24 is a perspective view of an exemplary anchor for the heart valve leaflet replacement system.

In another aspect, as shown in FIGS. 22 to 24, the distal portion 39 of the anchor can comprise a plurality of barbed segments that are curved at an acute angle with respect to the longitudinal axis of the anchor. In an exemplary aspect, the acute angle can be between about 45 and about 90 degrees. In a further aspect, the barbed segments can have a curved cross-sectional shape. In one aspect, the barbed segments can have a length of between about 3 and 5 mm.

As shown in FIG. 22, it is contemplated that the proximal portion 40 of the anchor can comprise solid rod structures.

As shown in FIGS. 23 and 24, the proximal portion 40 of the anchor can define one or more openings to allow for tissue ingrowth and neovascularization after implantation, to help the binding of the implanted anchor to the native tissue permanently, and thereby to prevent disengagement and dislodgment of the anchor. In this aspect, the anchors 30 can be configured to help the upper flared portion 13 of the stent 31 stay in a locked position for the entirety of its use. It is contemplated that the anchor 30 can be delivered in one or more steps to the native mitral annulus using a dilator coupled with a guide-wire and anchor delivery catheter. In this aspect, it is contemplated that the anchors 30 can be advanced into the formed hole in the mitral annulus, can be deployed by removing from the anchor from the anchor delivery catheter, and finally can be locked in position by pulling back on the tether portion 44.

Figure 25:
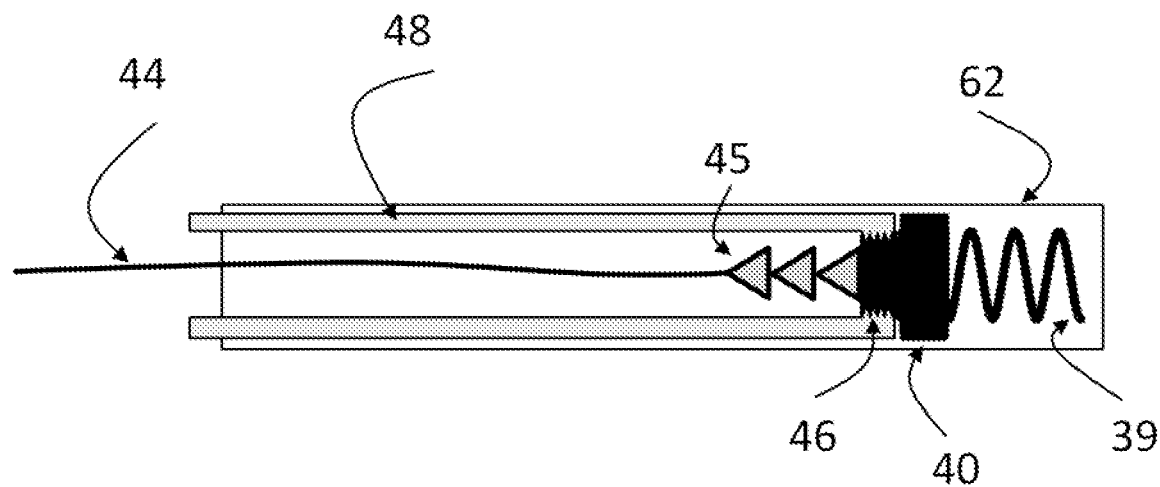
FIG. 25 is a cross-sectional view of an exemplary anchor delivery member for the heart valve leaflet replacement system, showing a portion of the anchor delivery catheter selectively coupled to a portion of the atrial side of an anchor.
Figure 26:
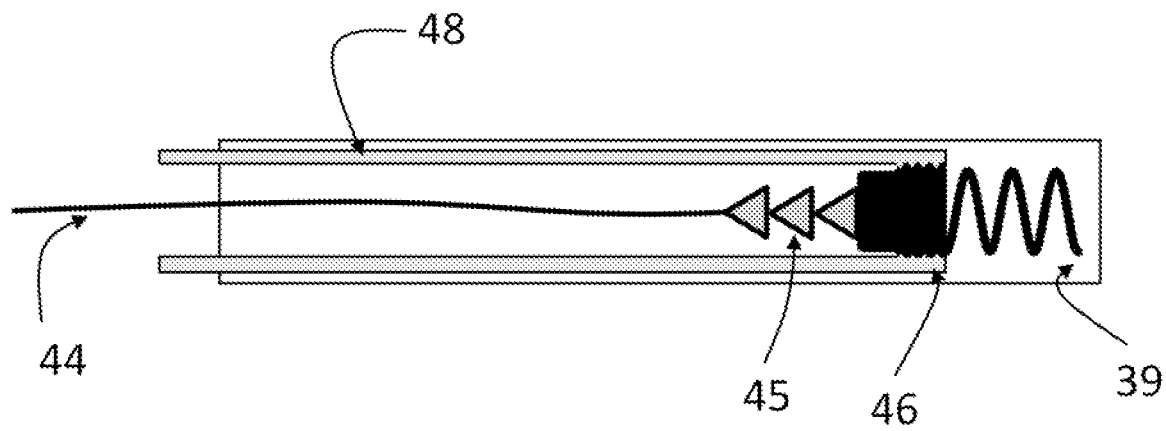
FIG. 26 is a cross-sectional view of an exemplary anchor delivery member for the heart valve leaflet replacement system, showing a portion of the anchor delivery catheter selectively coupled to a portion of the atrial side of an anchor.
Figures 27A, 27B, 27C:
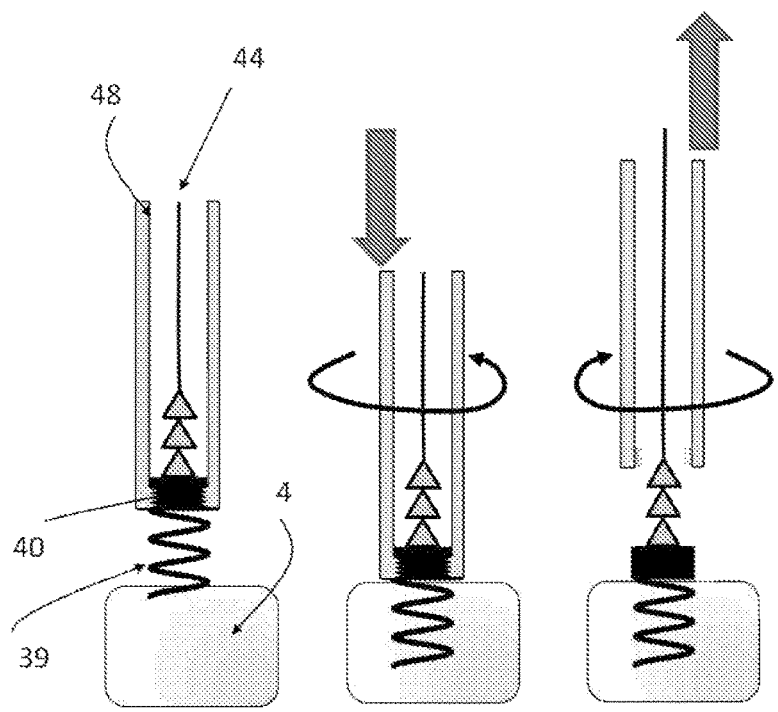
FIGS. 27A-27C are partial cross-sectional side views of an anchor being mounted at a desired location on the native mitral annulus.

Optionally, and referring now to FIGS. 25 to 26, the proximal portion 40 of the anchor can comprise a threaded surface 46 that is configured to be complementarily received within a threaded portion of an anchor delivery catheter 48. In this aspect, as exemplified in FIG. 27, it is contemplated that the coiled distal portion 39 of the anchor 30 could be implanted by rotating the anchor delivery catheter 48 in a first rotative direction. As one skilled in the art will appreciate, the anchor 30 can be subsequently separated from the threaded portion 46 of the anchor delivery catheter 48 by rotating the anchor delivery catheter in a second rotative direction that is opposite to the first rotative direction to unscrew the threaded surface of the proximal portion 40 of the anchor from the threaded portion of the anchor delivery catheter 48.

It is further contemplated that the elongated tether portion 44 can be configured to help position and secure the prosthetic mitral valve 12 to the implanted anchors 30. Optionally, it is contemplated that the tether portion 44 can be coupled to the proximal portion 40 of the anchor 30 and can be long enough to extend outside the patient's body, where it is connected to the lock delivery system. In another aspect, as exemplified in FIG. 28B, a portion of the tether adjacent to the proximal portion 40 of the anchor can have at least one male protrusion that is configured to facilitate locking of the tether within the locking device and thereby locking the stent 31 in the operative position. In one aspect, each male protrusion can be a formed by a knot in the tether material, or optionally by adding additional material to form a male protrusion. The tether portion 44 can be formed of, but not limited to, polymers, polytetrafluoroethylene (PTFE), metallic materials, or a combination of these materials.

Optionally, the tether 44 can comprise a suture-like section and a metallic section. In this aspect, it is contemplated that the suture-like section can be pre-attached to the proximal portion 40 of the anchor and the metallic section can be pre-attached to the suture-like section. The metallic section can be removed from the body following the implantation of the prosthetic mitral valve 12 while the suture-like section can remain in the body to secure the prosthetic mitral valve 12 to the mitral annulus.

In a further aspect, the method of delivering the prosthetic mitral valve 12 can be based on optional delivery access approaches. In one exemplary aspect and as described in more detail below, the method can entail a trans-septal access approach. In this aspect, an opening can be created in the internal jugular vein for the subsequent minimally invasive delivery of portions of the heart valve leaflet replacement system through the superior vena cava which flows into the right atrium of the heart. In this exemplary aspect, the delivery path crosses the atrial septum of the heart, and once achieved, the prosthetic mitral valve 12 of the heart valve leaflet replacement system can operatively access the left atrium 9, the native mitral valve, and the left ventricle 10. In this aspect, it is contemplated that the delivery path to the native mitral valve can be accessed trans-septally via a formed opening in the femoral vein, or the delivery path to the native mitral valve can be done trans-apically. In one aspect, it is contemplated that a main delivery catheter 62 can be placed along the delivery path to allow all of the delivery components of the heart valve leaflet replacement system 11 needed for the implant procedure to enter the left atrium 9 without complications.

In one aspect, a delivery catheter 62 can be configured for the delivery of the prosthetic mitral valve 12 to the previously implanted anchors 30. Prior to the deployment of the prosthetic mitral valve 12, the tether portions 44 extending from each of the anchors 30 can be passed through the openings 24 of the upper flared portion 13 of the prosthetic mitral valve 12.

Figure 30:
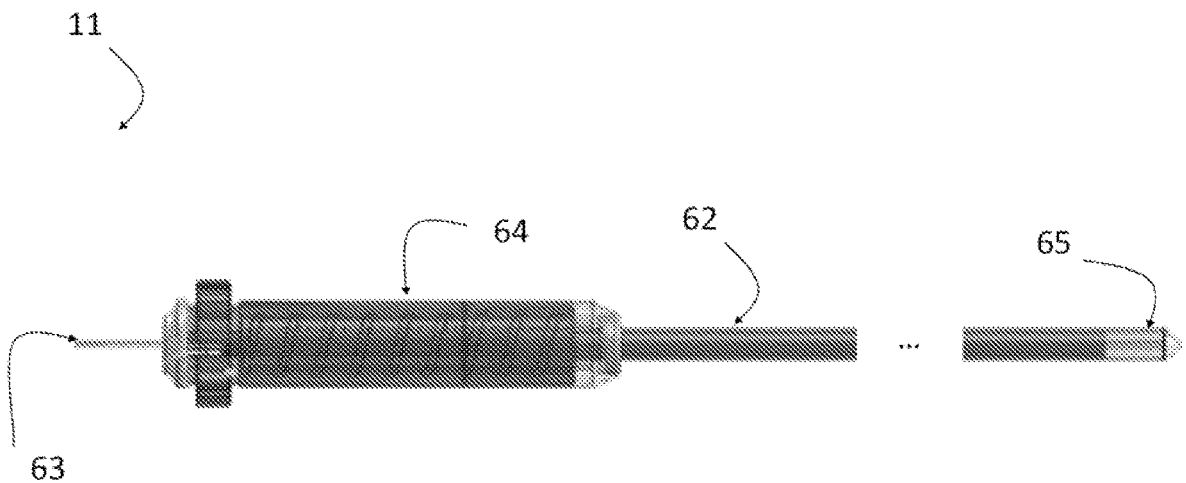
FIG. 30 is a side elevational view showing a steerable sheath and handle controller.

In one aspect, as exemplified in FIG. 30, a delivery catheter 62 can comprise a sheath that is attached to a selectively deflectable tip 65 that is configured to be selectively oriented. The delivery catheter 62 can further comprise a handle 64 that houses a guidewire 63 and conventional means for steering the deflectable tip 65.

Figure 44:
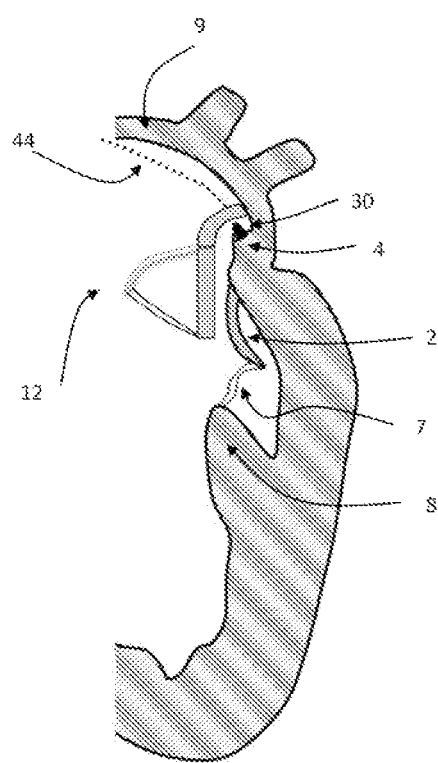
FIG. 44 is a schematic partial cross-sectional view showing an exemplary position of the deployed stent relative to the anchors prior to the stent being coupled to the plurality of anchors

Referring to FIG. 44, a plurality of anchors 30 can be sequentially implanted in the native mitral annulus. Subsequently, the prosthetic valve 12 can be delivered and positioned such that the upper flared portion 13 of the stent 31 can be in close proximity to the anchors 30. Optionally, it is contemplated that a method of retrieving the prosthetic valve 12 back into the delivery catheter 62 can be implemented to ensure the optimal delivery and positioning of the prosthetic valve replacement 12 inside the native mitral annulus.

In one aspect, it is contemplated that a two-step crimping procedure can be implemented to prepare the crescent shaped stent 31 into the compressed configuration within the valve catheter. In the first step, the two ends 26a,b of the crescent shaped stent can be joined together to form a full cylindrical shape by using a locking mechanism incorporated into the stent structure. The two ends 26a,b of the stent structure can have locking components, including but not limited to, hooks, teeth, and slots. In the second step, one end of the prosthetic valve can be squeezed and inserted into a series of cones and/or tubes until it reaches the desired crimping profile, then the prosthetic valve can be loaded into the delivery catheter 62. The prosthetic mitral valve 12 can be compressed using a transcatheter valve crimper.

The tether portion 44, extending from the proximal portion 40 of the anchors 30 and exiting the body, can pass through the openings 24 of the upper flared portion 13 prior to crimping of the prosthetic mitral valve 12. Then, the tethers 44 can be squeezed and crimped together with the prosthetic mitral valve 12. In this exemplary aspect and as one skilled in the art will appreciate, the tether portions 44 reside between the stent and the inner wall of the delivery catheter 75 can be twisted and tangled, thus, making it difficult to introduce the prosthetic valve to the native position. In order to smoothly slide the prosthetic valve 12 along the delivery catheter 62, it is contemplated that each tether portion 44 can be housed within a tubular catheter while being crimped with the prosthetic mitral valve 12. The tubular catheter can be made of stainless steel, Nitinol, Nylon, polyester, PTFE, EBAX (nylon co-polymer), PET, PUR, EVA, or custom blend materials and the like. It is further contemplated that the tubular catheter can be dimensioned to fit within the openings 24 of the upper flared portion 13 of the prosthetic mitral valve 12. The tubular catheter can extend to the distal end of the tethers 44 connected to the anchors 30 in the native valve to prevent the tangling of the tethers within the main delivery sheath 62. In operation, once the prosthetic mitral valve 12 is positioned at the tip 65 of the deflectable delivery sheath in the native left atrium 9, the tubular catheter can be removed prior to the release of the prosthetic mitral valve 12.

Figures 32A, 32B:
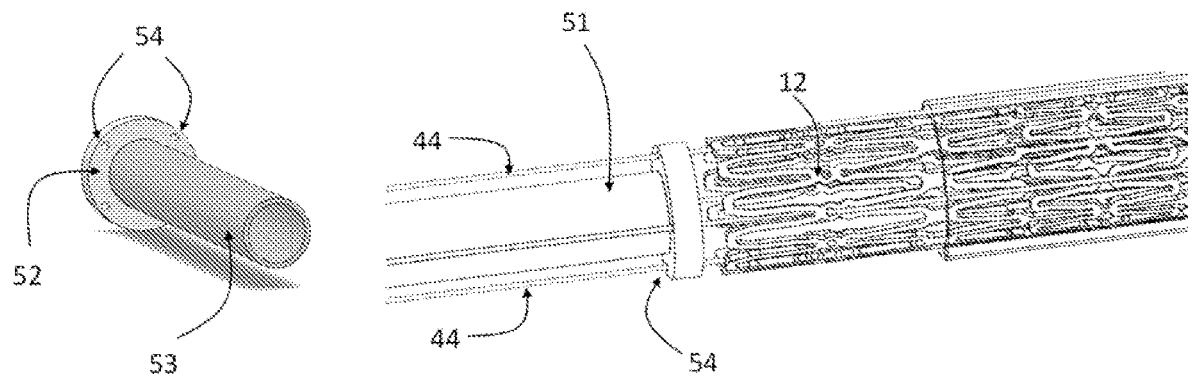
FIG. 32A-32B are a perspective views of the lock housing structure and its perspective location within the valve catheter.

The method of locking the stent 31 to the native annulus can be achieved using locking devices 70, as exemplified in FIG. 28, which can be attached to the tether portion 44. It is contemplated that the locking devices 70 can be delivered in individual succession or simultaneously after deploying the prosthetic mitral valve 12. It should be appreciated that by securing the prosthetic valve 12 using the locking devices 70, the annulus of the diseased valve can be reshaped to the shape of the prosthetic device 12 by pulling a plurality of tethers coupled to the anchors 30 which are already embedded in the native tissues. In one example for a dilated annulus, the distances between the anchors 30 on the annulus 4 will be larger than the distances between the hollow structures 24 on the upper flared portion 13 of the stent 31. Thus, pulling the tethers 44 while delivering the locking devices can draw or reduce the diameter of the dilated and diseased annulus. In this aspect, this system of placing a locking device at any preferred location along the tether allow marginal errors for placement of the anchors 30 on the annulus A lock housing structure 51, as exemplified in FIG. 32, can be subsequently loaded within the delivery sheath 62. In one aspect, the lock housing structure 51 can be configured to operatively house the tether(s) 44 and the lock delivering catheter(s) 57. In one aspect, the lock housing structure 51 can define a proximal portion 53 and a distal portion 52, where the distal portion 52 contains a plurality of lumens 54 for the tethers to pass through, as shown in FIG. 32A. The distal portion 52 is positioned adjacent to the upper flared portion 13 of the stent 31. Optionally, only a portion of the distal tip of the lock housing structure 51 can be configured to define the plurality of lumens 54 for the tethers 44 to pass through.

Figures 33A, 33B:
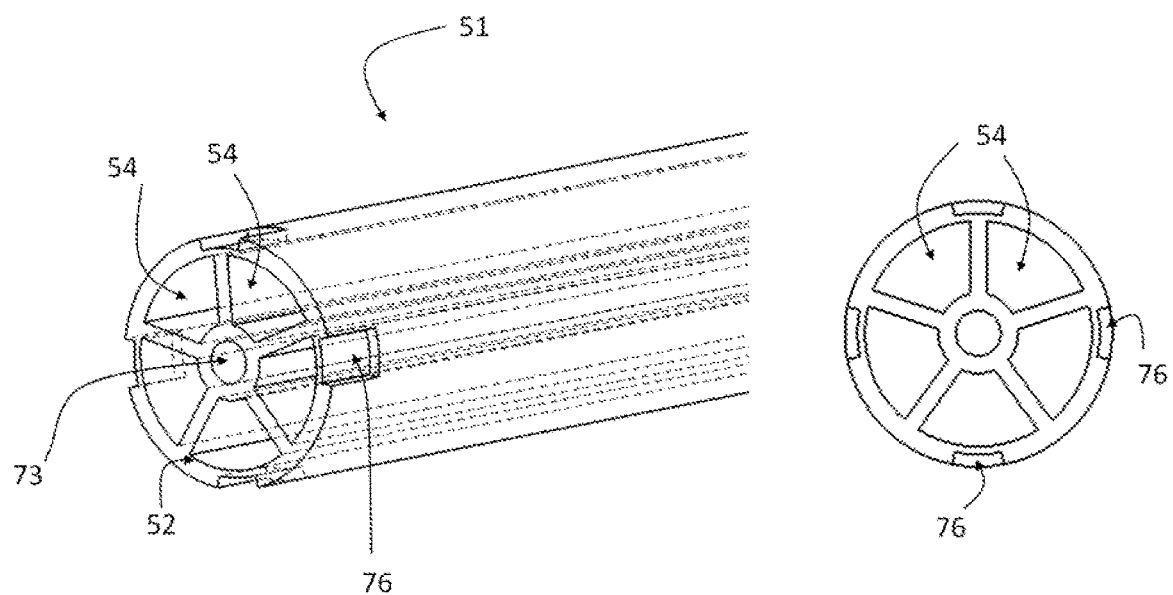
FIG. 33A-33B are views of the lock housing structure.

In another aspect, the lock housing structure catheter 51 can have a plurality of lumens 54 having a shape and configuration as illustrated in FIGS. 33A-33B. In this aspect, the dimensions of these lumens are configured to house the entire locking device delivery catheter 57. It is contemplated that two or more locking devices 70 could be delivered simultaneously upon the release of the prosthetic valve while rapid pacing is in place. Hence, the multiple lumen 54 of the lock housing structure 51 allow for two or more locking devices to be delivered rapidly.

Figure 31:
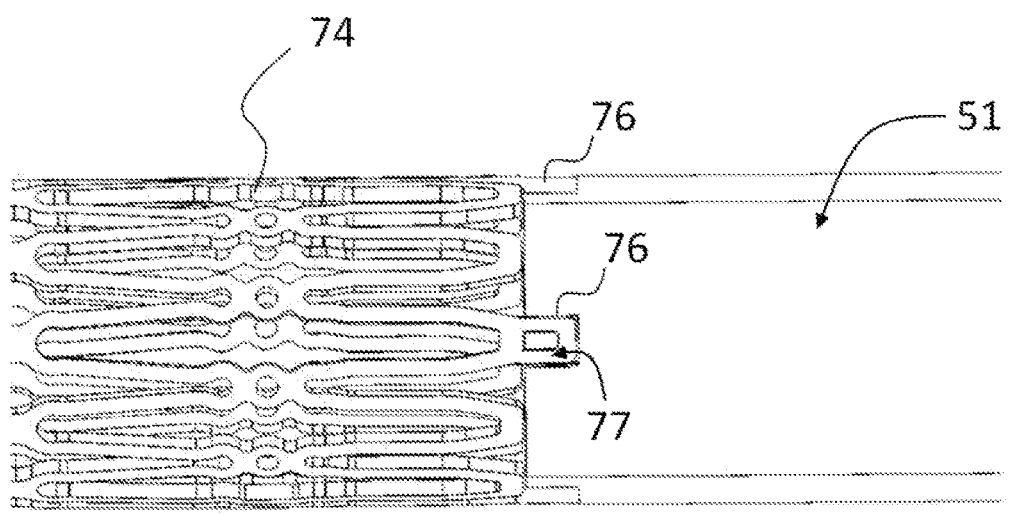
FIG. 31 is a side view of the crimped prosthetic device, showing the eyelets of the prosthetic device are being captured by the slots on the lock housing structure.
Figure 34:
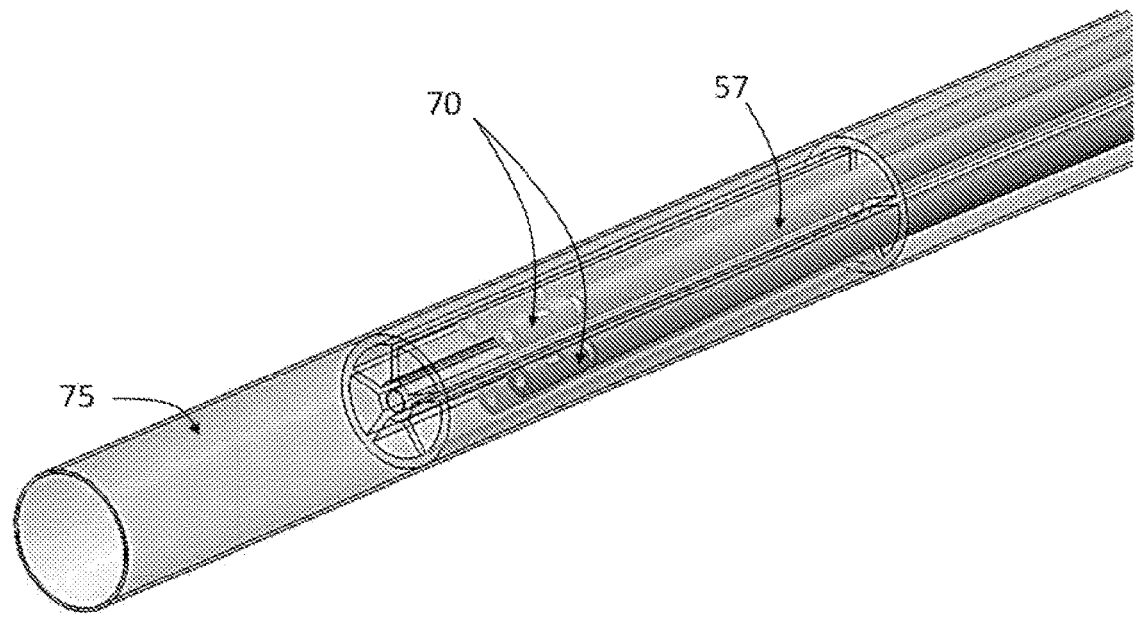
FIG. 34 is a perspective view of the valve catheter, showing the lock housing catheter and a plurality of locks and lock catheters.
Figure 35:
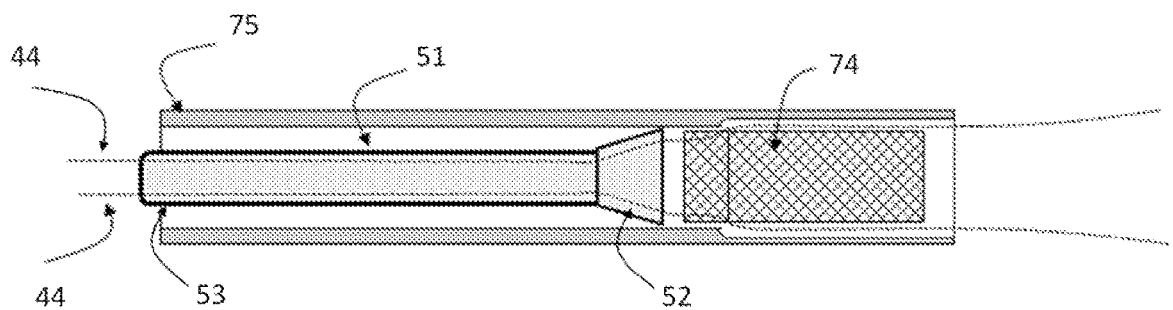
FIG. 35 is a cross-sectional view showing, positioned within a delivery catheter, a lock housing structure, a stent positioned in a compressed delivery position, and tether portions coupled to the stent.

Referring to FIG. 33, it is contemplated that the outer wall of the distal portion 52 of the lock housing structure 51 has two or more recesses 76 for insertion of two or more eyelets 77 of the stent. In this aspect, two or more eyelets 77 of the stent, as shown in FIG. 34, can be used to load the stent into the stent sheath 75. The crimped device 74, as exemplified in FIG. 31, can be subsequently loaded within the stent sheath 75. A cross sectional view of the lock housing structure 51, crimped stent 74, and tethers 44 is illustrated in FIG. 35.

It is contemplated that the locking device 70 can comprise a structure with a passage that allows at least one tether 44 to pass through. In a further aspect, the locking device 70 can be manipulated to be locked within a designated portion of the tether 44. In one aspect, the locking device 70 can be but not limited to a tubular structure, as exemplified in FIG. 28, which can clamp on to at least one of the tethers 44 using one or more tabs 59 extending radially inwards from the one side wall of the tubular structure and forming a tight contact against the opposite side of the tubular structure. The tethers 44 can have inline male protrusions that are configured to increase friction and axial resistance to prevent tether slippage. In this aspect, the tubular locking device 70 can be delivered and released using a locking delivery system.

In one aspect, the locking device 70 can be configured as a non-circular structure with passage for at least one tether to pass through. In an exemplary locking device, as exemplified in FIG. 28C, at least one tab is cut out and bent inwards from at least one flat side of the locking device. In this aspect, a tether 44 can form a tight contact against the side wall of the locking device. In a further aspect of this exemplary locking device, the edge of the tab 59 can be edged or electro-polished so that it will not cut into the tether.

Figures 28A, 28B, 28C, 28D:
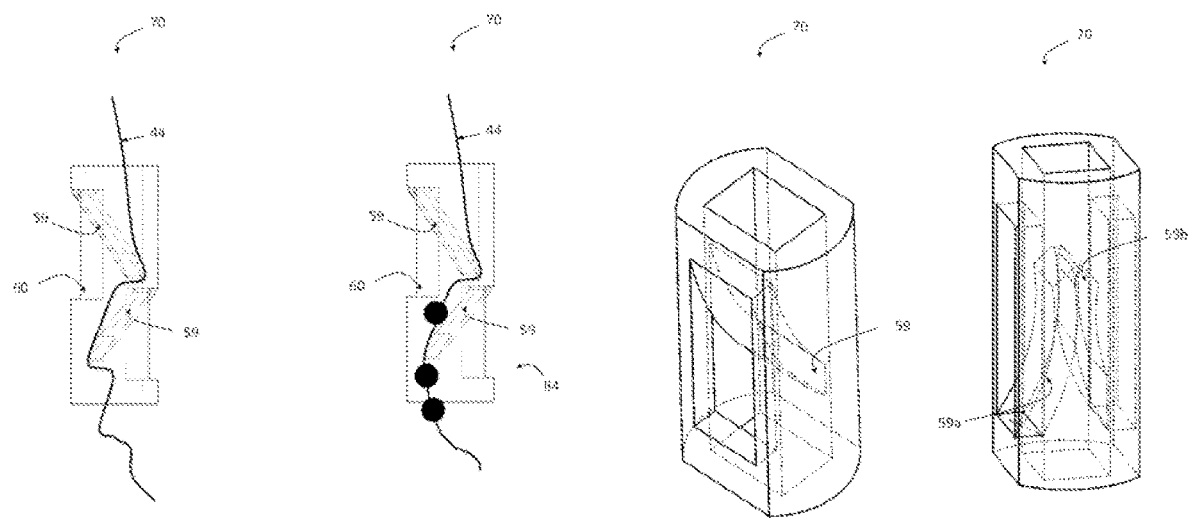
FIGS. 28A-28D are schematic views of an exemplary locking device.

In an additional aspect, the locking device 70 can be configured with two tabs 59, as exemplified in FIG. 28D, one on each side wall. The two tabs 59 are configured to bend inwards and meet at the center of the locking device 70. In this aspect, both tabs can press against the tether to allow tighter contact between the tether and the locking device.

Figure 29A:
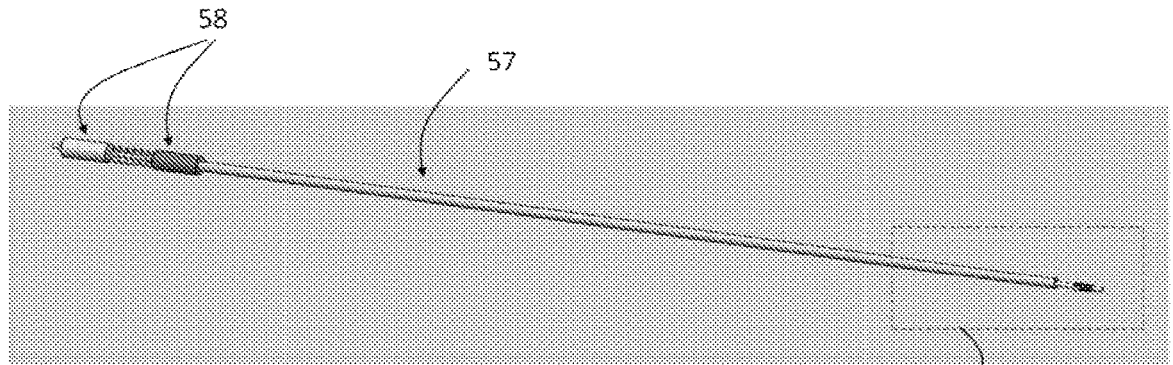
FIGS. 29A and 29B are schematic views of an exemplary locking device delivery system, showing a handle, catheter and the supporting catheter for the locking device.
Figure 29B:
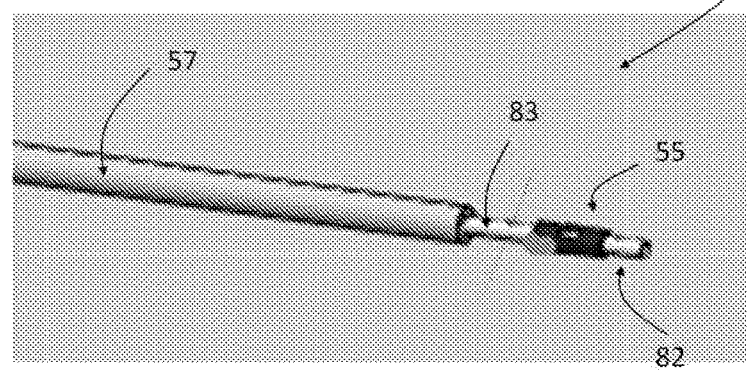

In one aspect, as shown in FIG. 34, the lock delivery components comprise a plurality of locks 70, a lock delivery catheter 57, a lock supporting tube 56, and a lock delivery catheter handle 58. In one aspect, the inner diameter of the locking device 70 can be slightly larger than the outer diameter of the supporting catheter 56, with little to no sliding between the two components. The lock supporting catheter 56 can comprise stiff 82 and flexible 83 portions. In this aspect, the stiff portion, as exemplified in FIG. 29, can be configured to open one or more tabs 59, i.e., push the tabs towards the wall of the locking device, to thereby allow the tether 44 to pass through thereby facilitating sliding of the locking device 70 along the tether 44. In this aspect, it will be appreciated that the flexible portion 83 of the lock supporting catheter 56 is configured to allow the catheter to flex and bend easily which will facilitate delivery of the locking device 70 at different locations around the annulus. In this aspect, the locking delivery catheter 58 is a flexible catheter, which can be conventionally operated to push the locking device 70 away from the stiff 82 portion of the locking supporting catheter 56 so that it can release the tabs 59 and couple to the tether 44 within the tubular structure of the locking device 70 to effectively lock the locking device into place along the tether 44. In a further aspect, the locking deliver catheter 58 can be tapered to a smaller diameter at the distal portion, adjacent to the locking devices 70, to facilitate the pushing and delivering of the locking devices 70.

In another aspect, the lock support catheter 56 can be configured as a single portion made of a single material. In this aspect, the lock support catheter 56 can be configured to be flexible, such configurations include but not limited to laser cutting a zig-zag pattern or a spiral cut through the wall.

Figure 36:
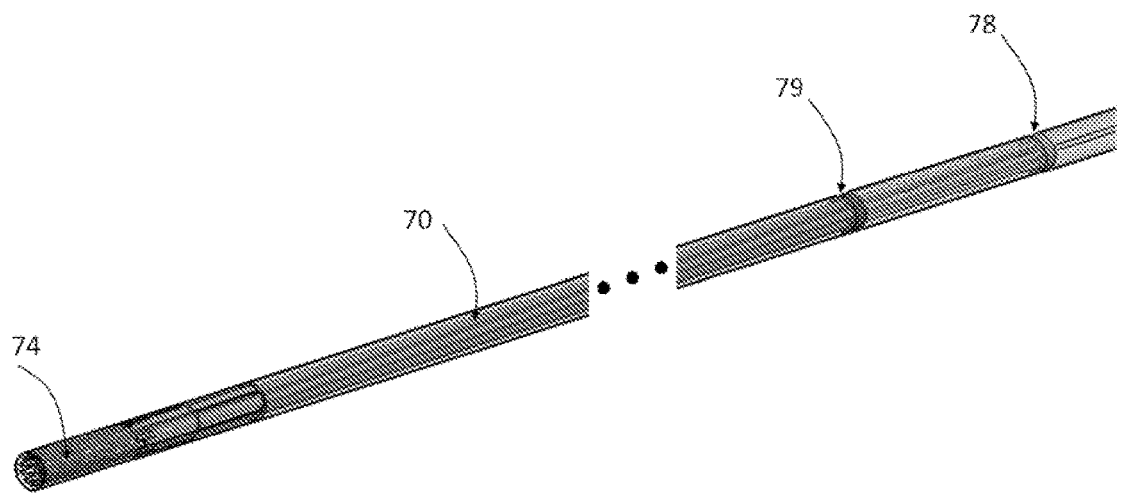
FIG. 36 is a perspective view of a first linking structure and a second linking structure, the first linking structure binding the lock delivery catheters and the second linking structures binding the lock supporting catheter.
Figure 37:
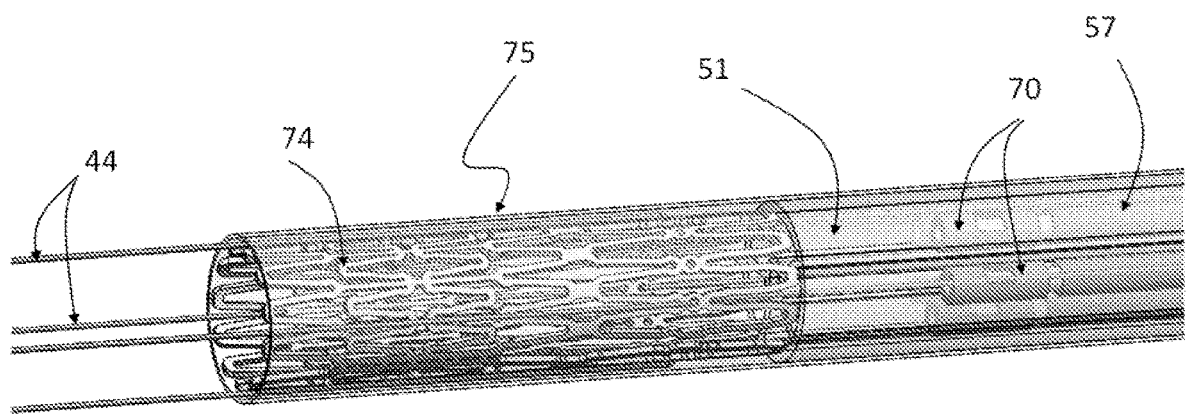
FIG. 37 is a perspective view of the valve catheter, showing a crimped prosthetic valve, a plurality of tethers, the lock housing structure, and a plurality of locks and lock catheters.

In an optional aspect, the delivery system can be configured such that all locks 70 are released simultaneously immediately after the release of the stent. In this aspect, it is contemplated that, as exemplified in FIG. 36, the locks 70 can be coupled together by a linkage mechanism, which can be a solid linking structure 78 with holes defined therein that is configured to secure and lock a plurality of the lock supporting catheters 56 in place. In this aspect, since the locks 70 also need to be released simultaneously, a second linkage structure 79 can also be configured to secure a plurality of lock delivery catheters 57. It is contemplated that both first and second linkage structures 78,79 can be configured to couple to the catheter system handle to enable simultaneous release with the stent.

Figure 38:
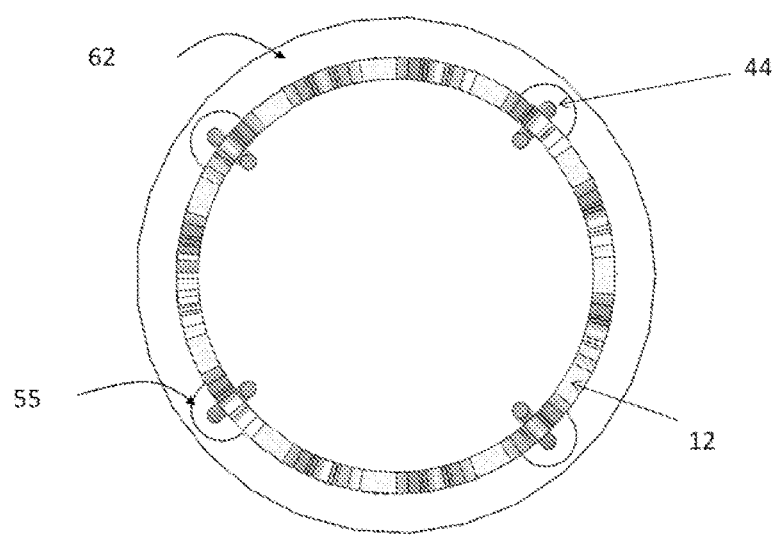
FIG. 38 is a cross-sectional view of the delivery catheter, showing a plurality of lumens that are configured to guide the tether portions coupled to the stent, and showing the stent positioned in the compressed delivery position.

Operatively, to help prevent the tangling of the tethers 44 with the stent 31 of the prosthetic mitral valve 12, the distal portion of the delivery sheath 62 can be configured to have at least four slots 55 formed within the delivery catheter sheath 62 that are each sized to accept a tether portion 44. FIG. 38 is a cross-sectional view of the delivery catheter 62 in which the stent of the prosthetic valve 12 is housed in the compressed position within a central lumen of the delivery sheath 62, and the slots 55 are formed in the wall thickness of the delivery sheath 62. It is further contemplated that the formed slots 55 can be evenly spaced or asymmetrically spaced inside the sheath to align with the housed stent 12.

Figure 47:
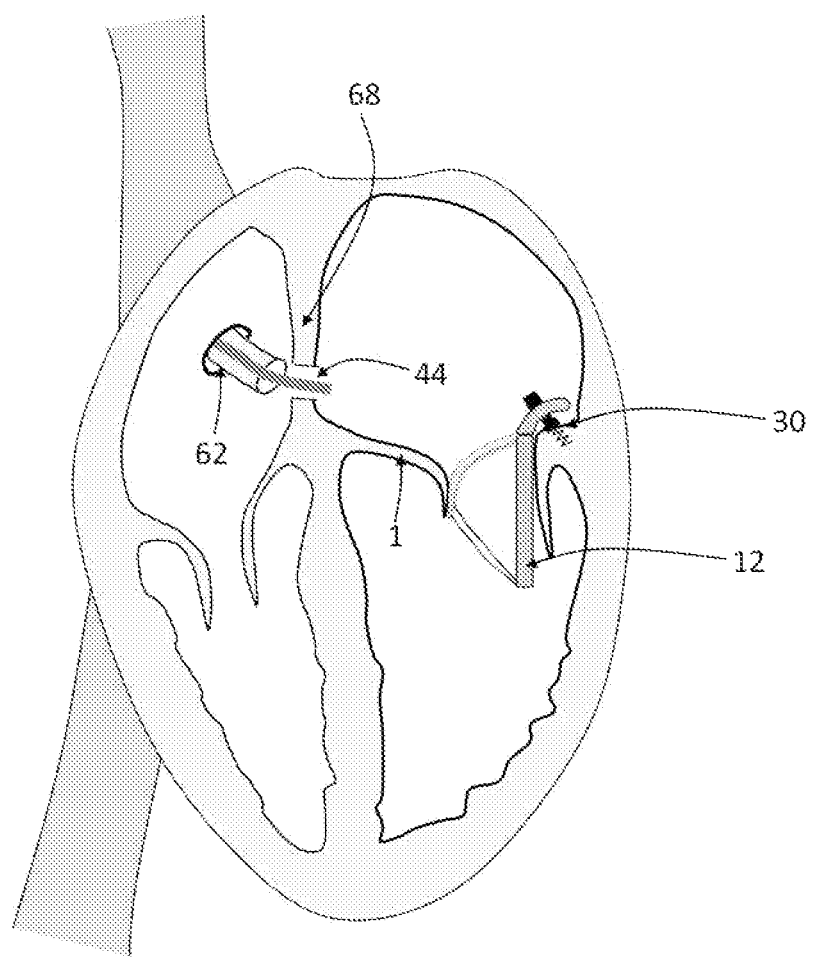
FIG. 47 is a schematic perspective view that shows the exemplary occlusion of the atrial septum. In this aspect, a septal occluder is introduced through the delivery catheter that extends through the atrial septum hole. Subsequently, the delivery catheter is withdrawn through the atrial septum hole and the septal occluder is pulled towards the atrial septum until the hole is securely occluded by the septal occluder.

Referring to FIG. 47, the prosthetic mitral valve 12 can be delivered to the native mitral valve from the internal jugular vein, via the superior vena cava 66 and across the atrial septum 68. In this exemplary method, a guidewire 63 can be inserted into the body through an incision in the internal jugular vein. The guidewire 63 is advanced along the internal jugular vein to the right atrium of the heart via the inferior vena cava 67.

Subsequently, the guidewire 63 is directed into the left atrium 9 by crossing the septal wall 68 and is then brought through the native mitral valve and positioned in the left ventricle 10. In this method, in an optional aspect, one or more dilators can then be advanced along the guidewire 63 to open the trans-septal perforation to allow the delivery catheter 62 to cross the septum 63.

Figure 39:
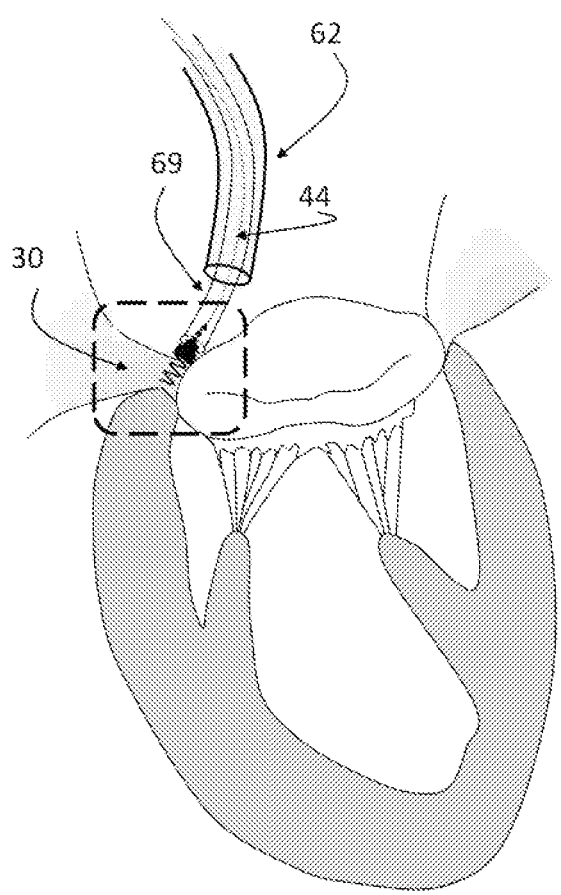
FIG. 39 is an exemplary schematic view of a plurality of anchors installed at spaced installation points on the native mitral annulus.
Figure 40:
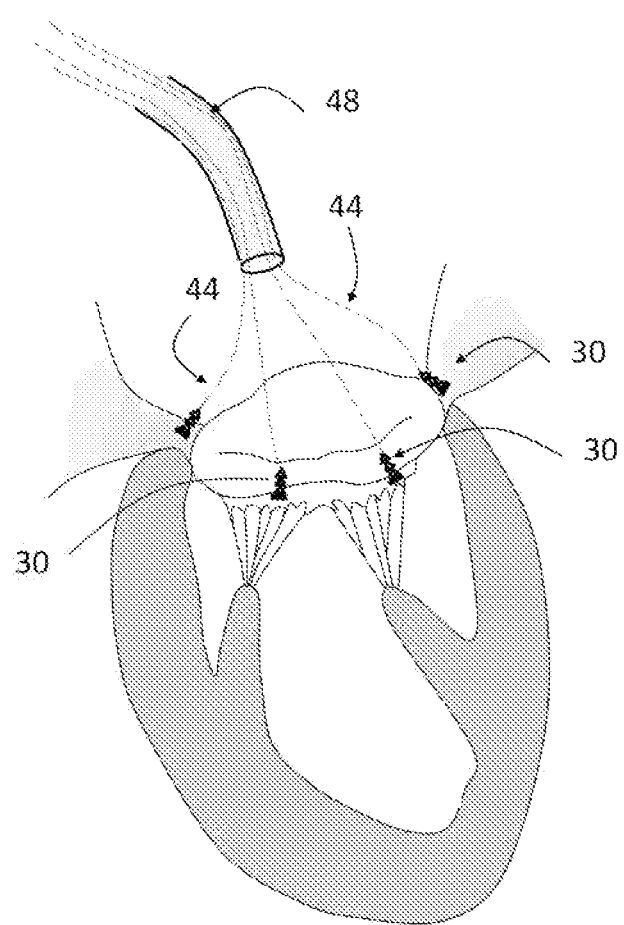
FIG. 40 is a schematic partial cross-sectional view showing a plurality of anchors implanted in the mitral annulus, and showing a tether portion coupled to each anchor that extends through the delivery catheter.

Once across the atrial septum 68, the tip 65 of the steerable catheter can be bent towards the first desired location within the mitral annulus for deploying the anchors 30, and the first anchor 30 is implanted at the first desired position, as exemplified in FIG. 39. In this aspect, it is preferred that the first desired location be located in either the left 6*b* or right trigone 6*a* regions. In one aspect, the preferred first desired location embodiment is in the left trigone 6*b*. Anchors 30 are sequentially delivered and implanted via the steerable catheter 69 until all of the desired anchors 30 are implanted therein the desired locations within the mitral annulus. When each anchor 30 is implanted, the anchor delivery catheter 48 is removed and the tether portion 44 is retained within the steerable delivery catheter 69, as exemplified in FIG. 40.

Figure 41:
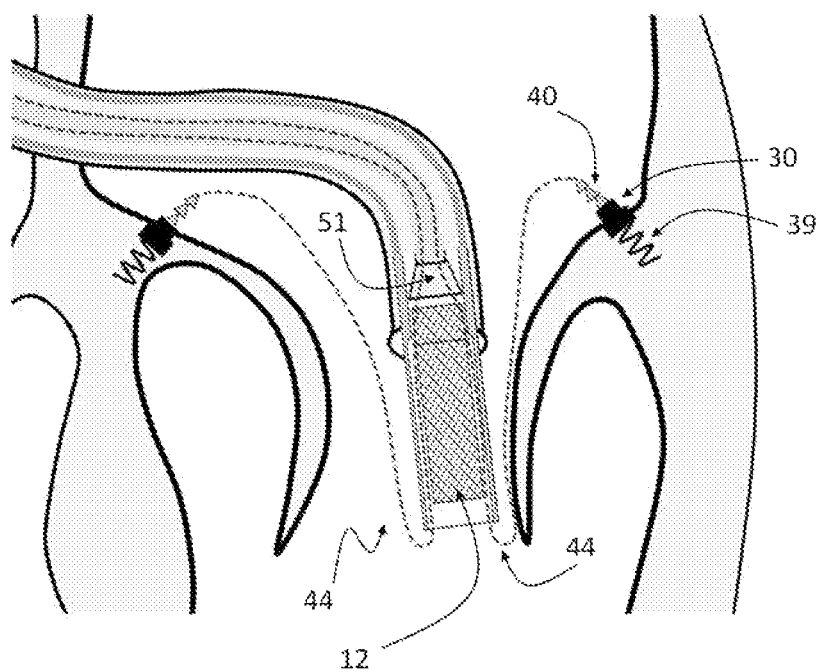
FIG. 41 is a schematic partial cross-sectional view showing the delivery catheter positioned inside the native mitral valve and a plurality of tethers coupled to respective anchors that extend from the delivery catheter.
Figure 42:
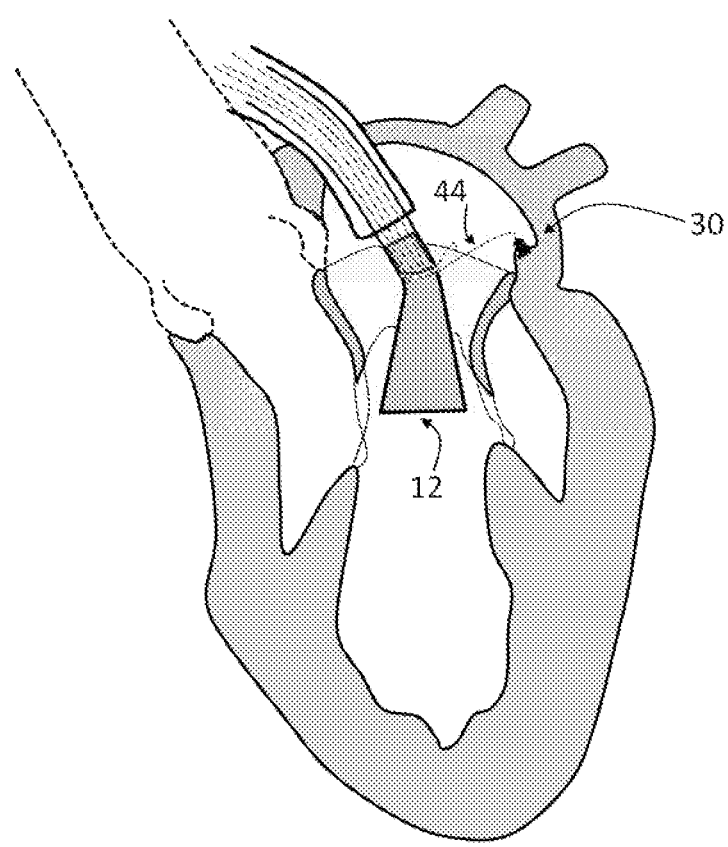
FIG. 42 is a schematic partial cross-sectional view showing the stent being deployed out of the catheter housing by advancing the lock housing structure.

During the subsequent prosthetic valve replacement deployment procedure, the tether portions 44 can be slightly tensioned to guide respective anchor pusher catheters 51 as they are advanced towards the prosthetic valve 12 to push the prosthetic valve 12 towards the anchors 30. FIG. 41 schematically illustrates positioning the prosthetic valve 12 at the native mitral valve. It is also contemplated that the prosthetic valve 12 deployment procedure can occur while rapid pacing is in place. In one exemplary view, shown in FIG. 42, the stent delivery sheath 75 can be selectively pushed outside the steerable tip 65 when the steerable tip of the delivery catheter is positioned next to the tip of the posterior leaflet or deep into the left ventricle.

Figure 43:
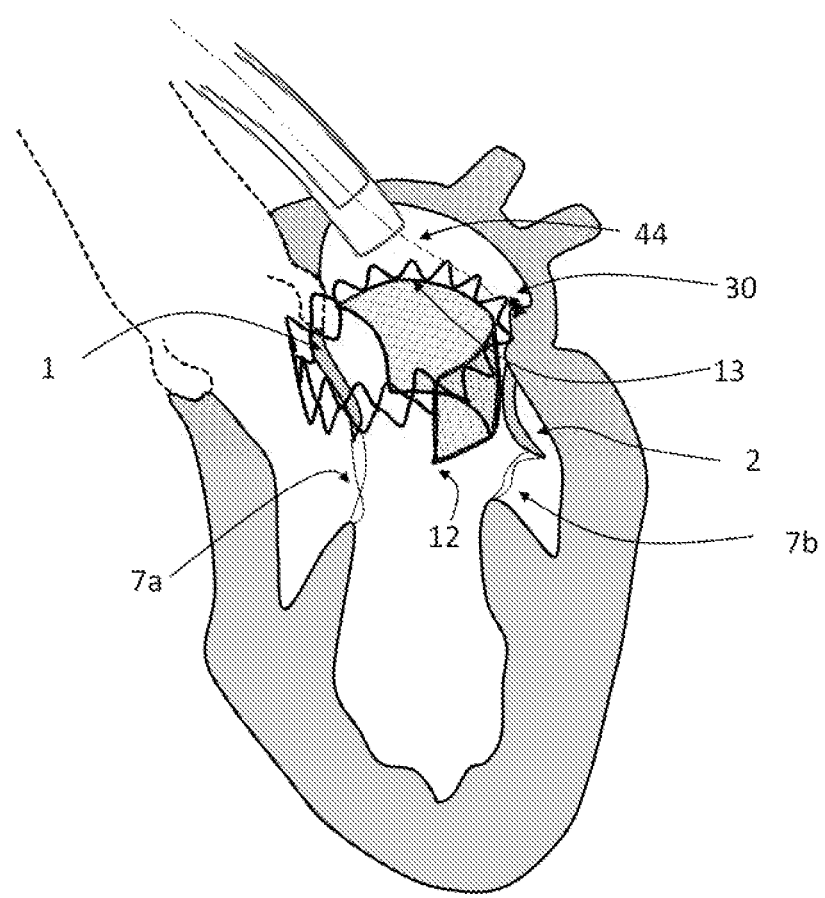
FIG. 43 is a schematic partial cross-sectional view showing the stent expanded to an operative position (without the prosthetic leaflets for the purpose of illustration) at the mitral annulus.

It is contemplated that the prosthetic mitral valve 12 can be delivered by pushing the lock housing structure catheter 51. Once the stent of the replacement prosthetic mitral valve 12 is fully ejected from the delivery sheath, the upper flared portion 13 of the prosthetic mitral valve 12 can operatively situate on top of the native annulus, as illustrated from different views in FIGS. 43 and 44.

In one aspect, it is contemplated that a two-step deployment procedure can be implemented to release the crescent shaped prosthetic mitral valve 12 into the normal functional configuration. In the first step, the prosthetic mitral valve 12 can be deployed into the left ventricle 10 at the level of the native mitral annulus, during which the prosthetic mitral valve 12 can maintain a full cylindrical shape with the locking mechanism of the two ends 26*a,b* still in place. The prosthetic mitral valve 12 can be oriented in a way that the markers on the stent structure can correspond to the two trigones 6*a,b* of the native mitral annulus. In the second step, the locking mechanism of the two ends 26*a,b* of the stent can be released and the prosthetic mitral valve 12 can be deployed into the designed semi-cylindrical shape to replace the native posterior mitral leaflet 2.

Subsequently, the stent of the prosthetic valve 12 can be locked in position relative to the native annulus by locking the anchors 30 to anchor openings of the upper flared portion 13 of the stent. By tensioning the anchor tethers 44 and locking the stent 31 in place by the anchors, the native annulus can be reshaped to the stent shape. It is contemplated that the means for locking the stent to the anchor 30 can provide flexibility so that the stent 31 of the prosthetic valve 12 can be locked in place at the annulus even when the anchors are deployed in a non-optimal configuration, i.e., when the anchors 30 are unevenly spaced or out of plane from each other.

In a further aspect, the stent 31 of the prosthetic valve 12 can be locked to the anchors simultaneously using the anchor delivery members. Pulling the tethers while slightly pushing the anchor delivery members can further reduce the annulus and allow the annulus to be cinched radially after locking the stent 31 in place.

In one aspect, the method of fixating the heart valve replacement system can be achieved by deploying the prosthetic valve 12 within a previously implanted docking station, consisting of a stent or structure meant to hold the heart valve replacement system in place, an annuloplasty band or ring, or a ventricular band or ring. It is contemplated that a heart valve leaflet replacement system that can be expanded to a larger diameter than the previously implanted device, can be deployed within the previously implanted device and provide enough frictional force to fixate the heart valve leaflet replacement system 12 in the operative position without the need for additional anchors or sutures.

Figure 46:
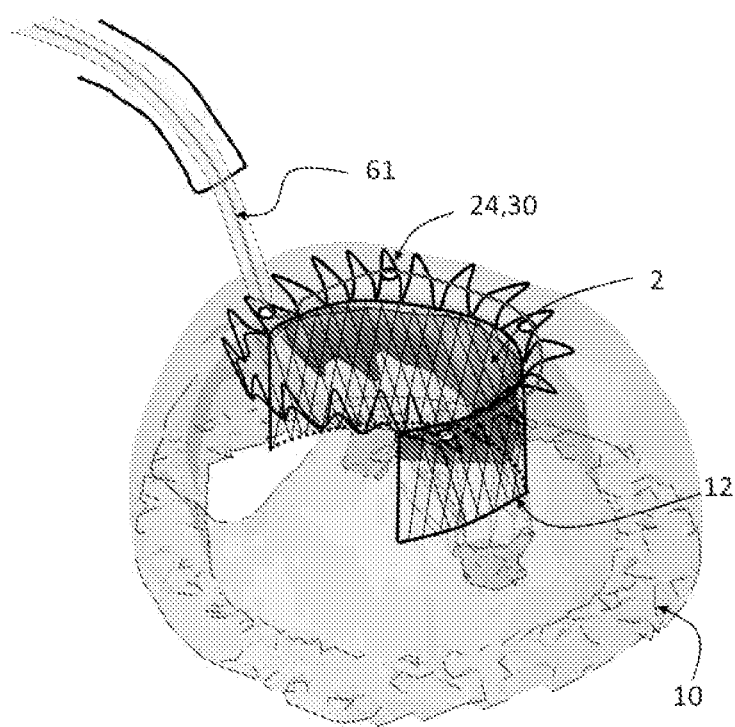
FIG. 46 is a schematic view of a suture running circumferentially through the stent structure at the level of the native mitral annulus such that the suture can be used to selectively cinch the mitral annulus.

In one aspect, an optional means for cinching the mitral annulus circumferentially is shown in FIG. 46. This means for cinching can entail a cinching tether 61 that extends circumferentially along the mitral annulus. In this aspect, an additional cinching tether 61 can be pre-attached to the upper flared portion 13 of the stent 31. Optionally, an additional cinching tether 61 can be pre-attached to the anchor(s) 30. Operationally, once the stent 31 of the prosthetic mitral valve 12 is locked to the anchors 30, the cinching procedure can be carried out. In one embodiment, the locking means of this cinching tether 61 can be of similar design to the means for locking the stent to the anchors 30.

In one aspect, as shown in FIG. 47, the methodology of delivering the prosthetic valve replacement can further comprise occluding the formed opening in the atrial septum 68 if necessary. Once the septum is successfully closed, the delivery catheter 62 can be removed from the body and the procedure is complete.

In one aspect, the prosthetic valve 12 can be configured to surgically replace a portion of the native valve. The upper flared portion 13 of the prosthetic valve 12 can also be configured to situate above the native annulus and be reinforced by suturing it to the native mitral annulus. In this aspect, it is contemplated that a plurality of stitches, such as, for example and without limitation, at least 4 stitches, at least 6 stitches, at least 8 stitches, and/or at least 4 to 10 stitches, are required to be placed within the annulus 4. All sutures can be spaced symmetrically along the posterior annulus 4. All sutures can extend about 1-3 mm from the leaflet-annulus junction or leaflet hinge. The first suture can be placed at the cleft between the anterior leaflet 1 and the posteromedial commissure 5b. The last suture can be placed at the cleft between the anterior leaflet 1 and anterolateral commissure 5a. Each end of the sutures can then pass through the upper flared portion 13 of the valve. Once all sutures are placed, the prosthetic valve 12 can be deployed in place. All sutures can be tied once the prosthetic valve 12 is well positioned.

Figure 48A:
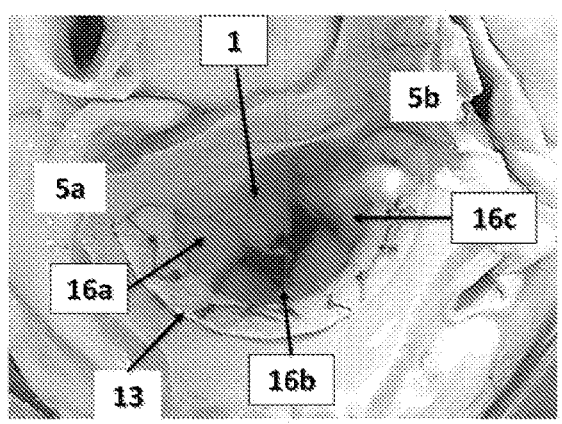
FIGS. 48A-48B are pictures taken from in vitro test of the valve prototype.
Figure 48B:
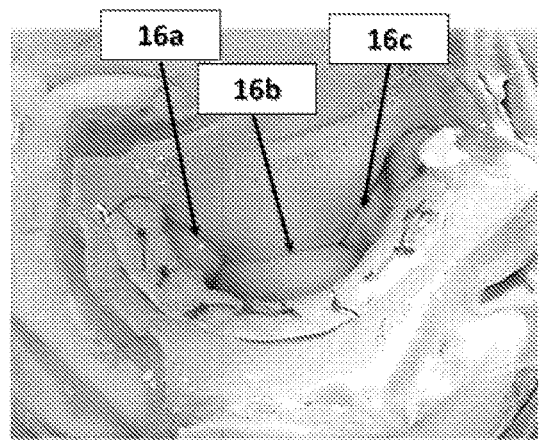

To further demonstrate the functionality of the prosthetic valve replacement device and system, ex vivo benchtop tests were performed using a pig heart. The prototype of the prosthetic valve 12 was implanted within the native mitral valve 1,2. The upper flared portion 13 of the stent 31 was sewn onto the annulus in an annuloplasty fashion. FIG. 48A shows the prosthetic valve positioned in a passive heart, with no pressure in the left ventricle. The prosthetic leaflets 16 and the native anterior leaflets 1 were free hanging. The two lateral edges 26a,b of the prosthetic valve were placed at the anterior 5a and posterior 5b commissures. The prosthetic valve did not cover the vicinity of the anterior mitral leaflet 1. FIG. 48B shows the prosthetic valve 12 positioned in a pressurized heart, with a pressure ranging between 100-120 mmHg within the enclosed left ventricle 10. The maximum pressure was developed using the static pressure test using an elevated water tank so that a pressure of 100-120 mmHg could be reached at the level of the left ventricle. The aorta was cannulated to allow inflow of water into the left ventricle. All three prosthetic leaflets 16 and the native anterior mitral leaflet 1 were visible upon pressurization. As shown, the prosthetic valve 12 successfully allowed proper coaptation of the leaflets, thereby preventing regurgitant flow. The prosthetic leaflets 16 coapted with the native anterior leaflet. A continuous coaptation line 71, (A1/16a, A2/16b, A3/16c), was visible from the top view. No paravalvular leakage was observed during pressurization.

Figure 49A:
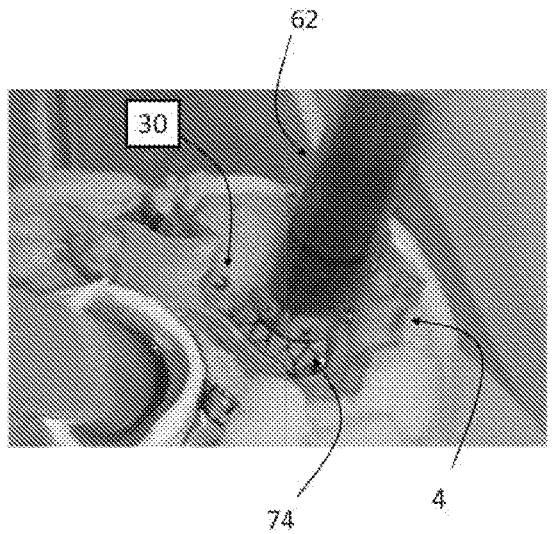
FIG. 49A-49B are pictures taken from in vitro tests of the prosthetic mitral valve prototype.
Figure 49B:
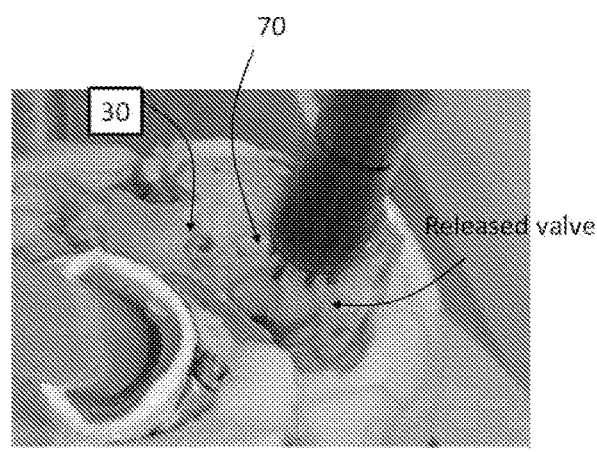
Figure 50A:
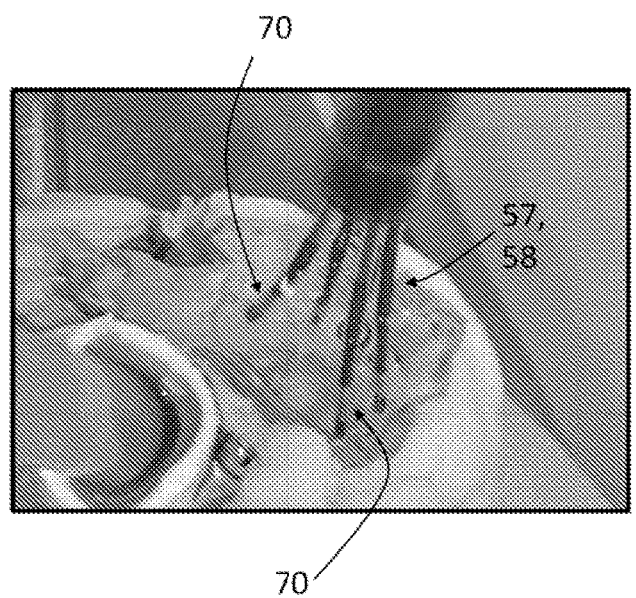
FIG. 50A-50B are pictures taken from in vitro tests of the prosthetic mitral valve prototype.
Figure 50B:
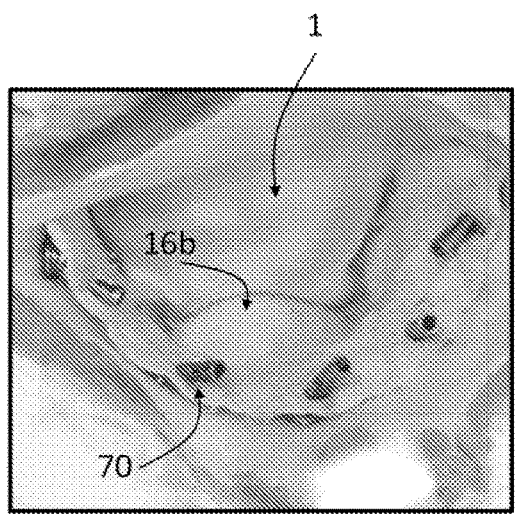

To demonstrate the functionality of the locking devices, ex vivo bench tests were performed using a pig heart. Prior to the prosthetic valve deployment, five anchors 30 were positioned within the mitral annulus using the anchor delivery catheters 48. The prosthetic valve 12 was then crimped onto a catheter 62 together with the locking assembly. The prosthetic valve was first released by retracting the valve catheter, as shown in FIG. 49A. Immediately after the valve was released in FIG. 49B, the lock catheters 57 were pushed out instantaneously, as shown in FIG. 50A. FIG. 50B was taken after release of the lock devices 70, and a pressure of 90 mmHg was applied, showing that the prosthetic valve 12 was securely anchored to the mitral annulus.

A surgical proof-of-concept of the device, shown in FIGS. 51A-51D, was demonstrated by testing in live animals (i.e., pigs). The primary safety endpoint was animal health and freedom from death. The secondary safety endpoint was freedom from device embolization or migration and no to trace mitral regurgitation (MR) grade after implantation at day 7 and 30. The primary safety endpoint was met in all tested animals (n=3). The secondary safety endpoint was met in two out of three animals. One prosthetic valve failure occurred in one animal where an oversized device was used, resulting in 2+MR (a regurgitant jet located at the anterolateral commissure) at day 30, the remaining two animals had trace to no MR and were clinically healthy. Hemodynamic evaluation was performed using computed tomography (CT), cardiac fluoroscopy, intracardiac echocardiogram (ICE), and transesophageal echocardiogram (TEE) on each animal after deployment at day 7 and day 30.

CT images consistently showed that the prosthetic leaflets 16 of the prosthetic valve 12 produced proper coaptation 71 with the native anterior mitral leaflet 1. The native anterior mitral leaflet 1 is divided into three scallops, A1, A2 and A3. A1 is at the anterolateral commissure and A3 is at the posteromedial commissure. The short axis views of the mitral valve at the level of the mitral annulus, in FIG. 51A, shows the native anterior 1 and posterior leaflets 2 revealed a clear coaptation line. Good coaptation 71 between all prosthetic leaflets 16 of the prosthetic valve 12 and of native heart valve leaflet 1 were further shown in FIGS. 51B-51D. FIG. 51B shows the native anterior leaflet 1 at A2 coapting with the prosthetic posterior leaflet 16b, FIG. 51C shows the native anterior leaflet 1 at A1 coapting with the prosthetic anterolateral commissure leaflet 16a, and FIG. 51D shows the native anterior leaflet 1 at A3 coapting with the prosthetic posteromedial commissure leaflet 16c. The stent frame 31 of the prosthetic valve 12 was clearly visible in these images, showing the upper flared portion 13 and the lower ventricular portion 14 positioning at the annulus 4 and within the left ventricle 10, respectively. There was no evidence of damage to the left ventricle from the stent frame of the prosthetic valve at 30 days.

Coaptation 71 of the prosthetic leaflets 16 and native leaflet 1 can be further illustrated in echocardiograms. The echocardiogram of the mitral valve in systole, FIG. 52, shows that the native anterior leaflet 1 at A2 can coapt with the prosthetic leaflet 16b and there was no obstruction of the LVOT by the prosthetic valve 12. Cardiac fluoroscopy, as shown in a series of images captured during left ventricular contraction in FIG. 53, was performed to detect regurgitant flow through the mitral valve. Little to no regurgitant volume was observed during mitral valve closure.

The early feasibility study of the prosthetic valve 12 showed that it could replicate the function of the native posterior leaflet 2. The data showed that upon prosthetic valve implantation, there was little to no MR in all but one animal in 30-day study. This prosthetic valve 12 could be used to replace the posterior leaflet of valves with MR, including but not limiting to, functional class of MR: type I MR with annular dilation or leaflet perforation/tear (normal leaflet motion), type II MR with papillary muscle and chordae tendineae rupture and/or elongated chordae tendineae (excessive leaflet motion), type IIIa MR with leaflet restriction motion in both diastole and systole due to mitral tissue thickening and fusion, and type IIIb MR with leaflet restriction motion in systole due to left ventricular enlargement leading to apico-lateral papillary muscle displacement and chordae tethering. Other etiologies of MR that this prosthetic valve 12 can be used including, but not limiting to, primary or degenerative MR.

It should be emphasized that the above-described aspects are merely possible examples of implementation, merely set forth a clear understanding of the principles of the present disclosure. Many variations and modifications can be made to the above-described embodiment(s) without departing substantially from the spirit and principles of the present disclosure. All such modifications and variations are intended to be included herein within the scope of the present disclosure, and all possible claims to individual aspects or combinations of elements or steps are intended to be supported by the present disclosure. Moreover, although specific terms are employed herein, as well as in the claims which follow, they are used only in a generic and descriptive sense, and not for the purposes of limiting the described invention, nor the claims which follow.

What is claimed is:

1. A prosthetic heart valve for treatment of a diseased heart valve having native anterior and posterior leaflets that move between an open configuration and a closed position to regulate blood flow through the heart valve during a cardiac cycle of a heart, the prosthetic heart valve comprising:
    a crescent shaped stent that is selectively expandable from a compressed position to an expanded, operative position; wherein the stent has an upper flared portion and a lower ventricular portion, wherein the upper flared portion is configured to overlie a posterior portion of the native annulus of the diseased heart valve, wherein at least a portion of the lower ventricular portion extends therefrom the upper flared portion and into the ventricular chamber of the heart, wherein at least a portion of the lower ventricular portion is configured to be positioned in contact with a portion of at least one native leaflet to displace the at least one native leaflet out of the blood flow upon expansion to the operative position; and
    a prosthetic pronged leaflet mounted on an inner surface of the stent, wherein the prosthetic pronged leaflet comprises a free edge, two commissure attachment regions, an attachment edge, a coaptation region, a belly region, and at least one hourglass shaped prong structure continuously extending from the free edge and configured to directly couple to the lower ventricular portion of the stent, wherein the prosthetic pronged leaflet is configured to be mobile throughout the cardiac cycle such that the prosthetic pronged leaflet coapts with a native leaflet when the valve is in the closed position to prevent the regurgitation of blood through the valve, wherein the prosthetic pronged leaflet is one-piece, and wherein the prosthetic pronged leaflet is mounted to the stent so that, in the operative position, a juncture of the prosthetic pronged leaflet and the stent forms a three dimensional leaflet-stent attachment curve,
    wherein the prosthetic heart valve comprises at least one characteristic selected from the group consisting of:
    (1) the three dimensional leaflet-stent attachment curve consists of three troughs;
    (2) the at least one hourglass shaped prong structure has a length of from 5.0 to 15.0 mm, and;
    (3) tip of the at least one hourglass shaped prong structure is at an angle of about 20°.

2. The prosthetic heart valve of claim 1, wherein the stent is radially collapsible and expandable.

3. The prosthetic heart valve of claim 2, wherein at least a portion of the upper flared portion and at least a portion of the lower ventricular portion is expandable to an operative position.

4. The prosthetic heart valve of claim 3, wherein, in the operative position, the upper flared portion spans an AC-anterior commissure and a PC-posterior commissure of the diseased heart valve.

5. The prosthetic heart valve of claim 2, wherein at least a portion of the upper flared portion and at least a portion of the lower ventricular portion is configured to reshape the native annulus.

6. The prosthetic heart valve of claim 1, wherein the prosthetic pronged leaflet is flexible and is configured to move between an open configuration and a closed position to regulate blood flow through the heart valve.

7. The prosthetic heart valve of claim 1, wherein the at least one hourglass shaped prong structure comprises a plurality of hourglass shaped prong structures.

8. The prosthetic heart valve of claim 1, wherein the upper flared portion defines a plurality of openings extending through the upper flared portion, and further comprising a means for anchoring the upper flared portion to the posterior portion of the native annulus.

9. The prosthetic heart valve of claim 8, wherein the means for anchoring comprises a plurality of anchors that are configured to be fixated therein the native annulus and, via the plurality of openings, to fixate the upper flared portion relative to the native annulus.

10. The prosthetic heart valve of claim 9, wherein each anchor comprises a distal portion and a proximal portion, wherein the distal portion of each anchor is configured to implant into the native annulus tissue and to resist separation after implantation.

11. The prosthetic heart valve of claim 10, wherein the proximal portion of the anchor defines a slot that is configured for attachment of a tether.

12. The prosthetic heart valve of claim 9, wherein each anchor further comprises an elongated tether portion that is configured to position and secure the prosthetic heart valve to the anchors.

13. The prosthetic heart valve of claim 1, wherein the stent has an inner and an outer surface, and further comprising a skirt that is coupled to at least a portion of the inner and/or outer surfaces of the stent.

14. The prosthetic heart valve of claim 13, wherein the attachment edge of the prosthetic pronged leaflet is attached to the stent at the skirt, and wherein the at least one hourglass shaped prong structure is attached to the stent at the skirt.

15. A prosthetic heart valve for treatment of a diseased heart valve having native anterior and posterior leaflets that move between an open configuration and a closed position to regulate blood flow through the heart valve during a cardiac cycle of a heart, the prosthetic heart valve comprising:
    a crescent shaped stent that is selectively expandable from a compressed position to an expanded, operative position; wherein the stent has an upper flared portion and a lower ventricular portion, wherein the upper flared portion is configured to overlie a posterior portion of the native annulus of the diseased heart valve, wherein, in the operative position, the upper flared portion spans the AC-anterior commissure and the PC-posterior commissure of the diseased heart valve, wherein at least a portion of the lower ventricular portion extends therefrom the upper flared portion and into the ventricular chamber of the heart, wherein at least a portion of the lower ventricular portion is positioned in contact with a portion of at least one native leaflet to displace at least one native leaflet out of the blood flow upon expansion to the operative position;

a means for anchoring the upper flared portion of the stent to the posterior portion of the native annulus;

at least one flexible prosthetic leaflet mounted on an inner surface of the stent, wherein the least one flexible prosthetic leaflet is configured to be mobile throughout the cardiac cycle such that the least one flexible prosthetic leaflet coapts with at least one native leaflet when the valve is in the closed position to prevent the regurgitation of blood through the valve; and at least one hourglass shaped prong structure configured to couple a portion of the at least one flexible prosthetic leaflet to the lower ventricular portion of the stent.

16. The prosthetic heart valve of claim 15, wherein the upper flared portion defines a plurality of openings extending through the upper flared portion.

17. The prosthetic heart valve of claim 16, wherein the means to anchoring comprises a plurality of anchors that are configured to be fixated therein the native annulus and to extend through the openings in the upper flared portion.

18. The prosthetic heart valve of claim 17, wherein each anchor comprises a distal portion and a proximal portion, wherein the distal portion of each anchor is configured to implant into the native annulus tissue and to resist separation after implantation.

19. The prosthetic heart valve of claim 18, wherein the proximal portion of the anchor defines a slot that is configured for attachment of a tether.

20. The prosthetic heart valve of claim 18, wherein each anchor further comprises an elongated tether portion that is configured to position and secure the prosthetic heart valve to the plurality of anchors.

21. The prosthetic heart valve of claim 20, wherein the at least one prosthetic leaflet is attached to the stent through the skirt, and wherein the at least one hourglass shaped prong structure is attached to the stent through the skirt.

22. The prosthetic heart valve of claim 17, wherein each anchor further comprises an elongated tether portion that is configured to position and secure a plurality of locking members to fixate the prosthetic heart valve in the operative position at the operatively positioned anchors.

23. The prosthetic heart valve of claim 15, wherein, in the operative position, the lower ventricular portion has a partial cylindrical shape.

24. The prosthetic heart valve of claim 15, wherein, in the operative position, the lower ventricular portion has a partial conical shape.

25. The prosthetic heart valve of claim 15, wherein the crescent shaped stent allows for the dynamic motion of the remaining native leaflet and for coaptation with the prosthetic leaflet.

26. The prosthetic heart valve of claim 15, wherein the at least one prosthetic leaflet is mounted on an inner surface of the lower ventricular portion of the stent.

27. The prosthetic heart valve of claim 15, wherein the stent has an inner and an outer surface, and further comprising a skirt that is coupled to at least a portion of the inner and/or outer surfaces of the stent.

28. The prosthetic heart valve of claim 15, wherein the at least one flexible prosthetic leaflet is mounted to the stent so that, in the operative position, a juncture of the at least one flexible prosthetic leaflet and the stent forms a three-dimensional leaflet-stent attachment curve that is configured to promote leaflet coaptation and provide leaflet stress reduction during the cardiac cycle.

29. A prosthetic heart valve for treatment of a diseased heart valve having native anterior and posterior leaflets that move between an open configuration and a closed position to regulate blood flow through the heart valve during a cardiac cycle of a heart, the prosthetic heart valve comprising:

a crescent shaped stent that is selectively expandable from a compressed position to an expanded, operative position; wherein the stent has an upper flared portion and a lower ventricular portion, wherein the upper flared portion is configured to overlie a posterior portion of the native annulus of the diseased heart valve, wherein at least a portion of the lower ventricular portion extends therefrom the upper flared portion and into the ventricular chamber of the heart, wherein at least a portion of the lower ventricular portion is configured to be positioned in contact with a portion of at least one native leaflet to displace the at least one native leaflet out of the blood flow upon expansion to the operative position;

a prosthetic pronged middle leaflet mounted on an inner surface of the stent; and a side commissure leaflet mounted on an inner surface of the stent on either side of the middle leaflet, wherein the prosthetic pronged middle leaflet comprises a free edge, two commissure attachment regions, an attachment edge, a coaptation region, a belly region, and at least one prong structure extending from the free edge and configured to directly couple to the lower ventricular portion of the stent, wherein the prosthetic pronged middle leaflet is configured to be mobile throughout the cardiac cycle such that the prosthetic pronged middle leaflet and side commissure leaflets coapt with a native leaflet when the valve is in the closed position to prevent the regurgitation of blood through the valve, and wherein the prosthetic pronged leaflet middle is mounted to the stent so that, in the operative position, a juncture of the prosthetic pronged middle leaflet and the stent forms a three dimensional leaflet-stent attachment curve.

30. The prosthetic heart valve of claim 29, wherein each side commissure leaflet is without prong structures.

31. A prosthetic heart valve for treatment of a diseased heart valve having native anterior and posterior leaflets that move between an open configuration and a closed position to regulate blood flow through the heart valve during a cardiac cycle of a heart, the prosthetic heart valve comprising:

a crescent shaped stent that is selectively expandable from a compressed position to an expanded, operative position; wherein the stent has an upper flared portion and a lower ventricular portion, wherein the upper flared portion is configured to overlie a posterior portion of the native annulus of the diseased heart valve, wherein at least a portion of the lower ventricular portion extends therefrom the upper flared portion and into the ventricular chamber of the heart, wherein at least a portion of the lower ventricular portion is configured to be positioned in contact with a portion of at least one native leaflet to displace the at least one native leaflet out of the blood flow upon expansion to the operative position;

a prosthetic pronged leaflet mounted on an inner surface of the stent, wherein the prosthetic pronged leaflet comprises a free edge, two commissure attachment regions, an attachment edge, a coaptation region, a belly region, and at least one hourglass shaped prong structure continuously extending from the free edge and configured to directly couple to the lower ventricular portion of the stent, wherein the prosthetic pronged leaflet is configured to be mobile throughout the cardiac cycle such that the prosthetic pronged leaflet coapts with a native leaflet when the valve is in the closed position to prevent the regurgitation of blood through the valve, and wherein the prosthetic pronged leaflet is mounted to the stent so that, in the operative position, a juncture of the prosthetic pronged leaflet and the stent forms a three dimensional leaflet-stent attachment curve;

a plurality of openings extending through the upper flared portion; and a plurality of anchors that are configured to be fixated within the native annulus and, via the plurality of openings, to fixate the upper flared portion relative to the native annulus.

* * * * *